(12) United States Patent
Eberl

(10) Patent No.: US 7,785,324 B2
(45) Date of Patent: Aug. 31, 2010

(54) CLAMP BASED LESION FORMATION APPARATUS AND METHODS CONFIGURED TO PROTECT NON-TARGET TISSUE

(75) Inventor: Greg Eberl, Sunnyvale, CA (US)

(73) Assignee: Endoscopic Technologies, Inc. (ESTECH), San Ramon, CA (US)

( * ) Notice: Subject to any disclaimer, the term of this patent is extended or adjusted under 35 U.S.C. 154(b) by 714 days.

(21) Appl. No.: 11/067,535

(22) Filed: Feb. 25, 2005

(65) Prior Publication Data

US 2006/0195080 A1 Aug. 31, 2006

(51) Int. Cl.
*A61B 18/12* (2006.01)
(52) U.S. Cl. ............................ 606/49; 606/41; 606/52
(58) Field of Classification Search ............... 606/41, 606/51–52, 48, 45, 49
See application file for complete search history.

(56) References Cited

U.S. PATENT DOCUMENTS

| 463,785 | A | 11/1891 | Connable |
| 1,586,654 | A | 6/1926 | Bierman |
| 2,743,726 | A | 5/1956 | Grieshaber |
| 3,174,309 | A | 3/1965 | Kobayashi |
| 3,316,913 | A | 5/1967 | Swenson |
| 3,503,398 | A | 3/1970 | Fogarty et al. |
| 3,802,437 | A | 4/1974 | Kees, Jr. |
| 3,831,607 | A | 8/1974 | Lindemann |
| 3,920,021 | A | 11/1975 | Hittebrandt |
| 3,999,555 | A | 12/1976 | Person |
| 4,120,302 | A | 10/1978 | Ziegler |
| 4,201,213 | A | 5/1980 | Townsend |
| 4,306,561 | A | 12/1981 | De Medinaceli |
| 4,567,890 | A | 2/1986 | Ohta |
| 4,685,459 | A | 8/1987 | Koch |
| 4,819,633 | A | 4/1989 | Bauer |
| 4,821,719 | A | 4/1989 | Fogarty |
| 4,834,090 | A | 5/1989 | Moore |
| 4,924,864 | A | 5/1990 | Danzig |
| 4,985,030 | A | 1/1991 | Melzer |
| 5,002,561 | A | 3/1991 | Fisher |
| 5,100,388 | A | 3/1992 | Behl et al. |
| 5,122,139 | A * | 6/1992 | Sutter ..................... 606/51 |
| 5,131,379 | A | 7/1992 | Sewell |
| 5,147,357 | A | 9/1992 | Rose |
| 5,151,102 | A | 9/1992 | Kamiyama |

(Continued)

FOREIGN PATENT DOCUMENTS

EP 106748 A1 4/1984

(Continued)

OTHER PUBLICATIONS

Office Action dated Jan. 30, 2008, for Japanese Patent Application No. 2003-569081, filed Nov. 25, 2002, Applicant: Boston Scientific Limited (5 pages).

(Continued)

*Primary Examiner*—Linda C Dvorak
*Assistant Examiner*—Jaymi Della
(74) *Attorney, Agent, or Firm*—Townsend and Townsend and Crew LLP

(57) ABSTRACT

Apparatus, systems and methods for forming lesions in target tissue and positioning an insulation element adjacent to non-target tissue.

19 Claims, 18 Drawing Sheets

U.S. PATENT DOCUMENTS

| | | |
|---|---|---|
| 5,190,541 A | 3/1993 | Abele |
| 5,250,072 A | 10/1993 | Jain |
| 5,282,812 A | 2/1994 | Suarez |
| 5,290,286 A | 3/1994 | Parins |
| 5,300,065 A | 4/1994 | Anderson |
| 5,300,087 A | 4/1994 | Knoepfler |
| 5,318,564 A | 6/1994 | Eggers |
| 5,324,288 A | 6/1994 | Billings |
| 5,370,650 A | 12/1994 | Tovey |
| 5,398,683 A | 3/1995 | Edwards |
| 5,441,483 A | 8/1995 | Avitall |
| 5,443,463 A | 8/1995 | Stern |
| 5,445,638 A | 8/1995 | Rydell |
| 5,450,846 A | 9/1995 | Goldreyer |
| 5,456,682 A | 10/1995 | Edwards et al. |
| 5,476,479 A | 12/1995 | Green |
| 5,484,435 A | 1/1996 | Fleenor |
| 5,496,312 A | 3/1996 | Klicek |
| 5,518,164 A | 5/1996 | Hooven |
| 5,540,684 A | 7/1996 | Hassler, Jr. |
| 5,545,193 A | 8/1996 | Fleischman |
| 5,546,682 A | 8/1996 | Skerry |
| 5,569,274 A | 10/1996 | Rapacki |
| 5,571,121 A | 11/1996 | Heifetz |
| 5,575,810 A | 11/1996 | Swanson |
| 5,582,609 A | 12/1996 | Swanson et al. |
| 5,599,350 A | 2/1997 | Schulze |
| 5,624,454 A | 4/1997 | Palti |
| 5,626,607 A | 5/1997 | Malecki |
| 5,637,090 A | 6/1997 | McGee |
| 5,667,517 A | 9/1997 | Hooven |
| 5,673,695 A | 10/1997 | McGee |
| 5,693,051 A | 12/1997 | Schulze |
| 5,707,369 A | 1/1998 | Vaitekunas |
| 5,746,748 A | 5/1998 | Steinberg |
| 5,755,715 A | 5/1998 | Stern et al. |
| 5,766,166 A | 6/1998 | Hooven |
| 5,776,130 A | 7/1998 | Buysse |
| 5,782,899 A | 7/1998 | Imran |
| 5,797,905 A | 8/1998 | Fleischman et al. |
| 5,824,005 A | 10/1998 | Motamedi |
| 5,833,690 A | 11/1998 | Yates |
| 5,843,101 A | 12/1998 | Fry |
| 5,846,239 A | 12/1998 | Swanson et al. |
| 5,888,198 A | 3/1999 | Eggers et al. |
| 5,891,095 A | 4/1999 | Eggers et al. |
| 5,891,140 A | 4/1999 | Ginn |
| 5,908,420 A | 6/1999 | Parins |
| 5,925,038 A | 7/1999 | Panescu et al. |
| 5,938,694 A | 8/1999 | Jaraczewski |
| 5,951,549 A | 9/1999 | Richardson |
| 5,961,513 A | 10/1999 | Swanson et al. |
| 5,971,983 A | 10/1999 | Lesh |
| 6,004,269 A | 12/1999 | Crowley |
| 6,004,320 A | 12/1999 | Casscells |
| 6,010,500 A | 1/2000 | Sherman et al. |
| 6,010,516 A | 1/2000 | Hulka |
| 6,012,457 A | 1/2000 | Lesh |
| 6,022,313 A | 2/2000 | Ginn |
| 6,023,638 A | 2/2000 | Swanson |
| 6,039,748 A | 3/2000 | Savage |
| 6,050,996 A | 4/2000 | Schmaltz |
| 6,056,747 A | 5/2000 | Saadat |
| 6,071,279 A | 6/2000 | Whayne |
| 6,076,012 A | 6/2000 | Swanson |
| 6,086,586 A | 7/2000 | Hooven |
| 6,096,033 A | 8/2000 | Tu |
| 6,113,596 A | 9/2000 | Hooven |
| 6,115,626 A | 9/2000 | Whayne |
| 6,139,563 A | 10/2000 | Cosgrove |
| 6,142,994 A | 11/2000 | Swanson et al. |
| 6,152,899 A | 11/2000 | Farley |
| 6,152,920 A | 11/2000 | Thompson |
| 6,161,543 A | 12/2000 | Cox |
| 6,162,220 A | 12/2000 | Nezhat |
| 6,164,283 A | 12/2000 | Lesh |
| 6,174,309 B1 | 1/2001 | Wrublewski |
| 6,179,837 B1 | 1/2001 | Hooven |
| 6,210,330 B1 | 4/2001 | Tepper |
| 6,228,104 B1 | 5/2001 | Fogarty |
| 6,237,605 B1 | 5/2001 | Vaska |
| 6,245,068 B1 | 6/2001 | Olson et al. |
| 6,267,761 B1 | 7/2001 | Ryan |
| 6,273,887 B1 | 8/2001 | Yamauchi et al. |
| 6,273,902 B1 | 8/2001 | Fogarty |
| 6,277,117 B1 | 8/2001 | Tetzlaff |
| 6,288,104 B1 | 9/2001 | Gericke et al. |
| 6,290,699 B1 | 9/2001 | Hall |
| 6,296,640 B1 | 10/2001 | Wampler |
| 6,308,104 B1 | 10/2001 | Taylor |
| 6,311,692 B1 | 11/2001 | Vaska |
| 6,312,426 B1 | 11/2001 | Goldberg |
| 6,314,962 B1 | 11/2001 | Vaska |
| 6,314,963 B1 | 11/2001 | Vaska |
| 6,325,797 B1 | 12/2001 | Stewart |
| 6,330,473 B1 | 12/2001 | Swanson et al. |
| 6,334,861 B1 | 1/2002 | Chandler |
| 6,350,264 B1 | 2/2002 | Hooven |
| 6,352,536 B1 | 3/2002 | Buysse |
| 6,387,112 B1 | 5/2002 | Fogarty |
| 6,395,325 B1 | 5/2002 | Hedge et al. |
| 6,416,508 B1 | 7/2002 | Eggers et al. |
| 6,432,103 B1 | 8/2002 | Ellsberry et al. |
| 6,440,130 B1 | 8/2002 | Mulier |
| 6,443,952 B1 | 9/2002 | Mulier |
| 6,454,766 B1 | 9/2002 | Swanson et al. |
| 6,464,699 B1 | 10/2002 | Swanson |
| 6,464,700 B1 | 10/2002 | Koblish et al. |
| 6,468,272 B1 | 10/2002 | Koblish |
| 6,471,699 B1 | 10/2002 | Fleischman |
| 6,488,680 B1 | 12/2002 | Francischelli et al. |
| 6,511,480 B1 | 1/2003 | Tetzlaff |
| 6,514,250 B1 | 2/2003 | Jahns |
| 6,517,536 B2 | 2/2003 | Hooven |
| 6,522,905 B2 | 2/2003 | Desai |
| 6,522,930 B1 | 2/2003 | Schaer et al. |
| 6,527,767 B2 * | 3/2003 | Wang et al. .................. 606/32 |
| 6,529,756 B1 | 3/2003 | Phan et al. |
| 6,533,784 B2 | 3/2003 | Truckai et al. |
| 6,542,781 B1 | 4/2003 | Koblish et al. |
| 6,544,262 B2 | 4/2003 | Fleischman |
| 6,558,408 B1 | 5/2003 | Fogarty et al. |
| 6,582,429 B2 | 6/2003 | Krishnan et al. |
| 6,584,360 B2 | 6/2003 | Francischelli et al. |
| 6,595,991 B2 | 7/2003 | Tollner et al. |
| 6,610,055 B1 | 8/2003 | Swanson et al. |
| 6,632,220 B1 | 10/2003 | Eggers et al. |
| 6,645,202 B1 | 11/2003 | Pless et al. |
| 6,663,622 B1 | 12/2003 | Foley |
| 6,679,882 B1 | 1/2004 | Kornerup |
| 6,685,715 B2 | 2/2004 | Danitz et al. |
| 6,692,491 B1 | 2/2004 | Phan |
| 6,692,514 B2 | 2/2004 | Fogarty et al. |
| 6,706,038 B2 | 3/2004 | Francischelli et al. |
| 6,770,071 B2 | 8/2004 | Woloszko et al. |
| 6,771,996 B2 | 8/2004 | Bowe et al. |
| 6,780,180 B1 | 8/2004 | Goble et al. |
| 6,786,905 B2 | 9/2004 | Swanson et al. |
| 6,807,968 B2 | 10/2004 | Francischelli et al. |
| 6,837,877 B2 | 1/2005 | Zurcher |
| 6,837,887 B2 | 1/2005 | Woloszko et al. |
| 6,887,238 B2 | 5/2005 | Jahns |
| 6,889,694 B2 | 5/2005 | Hooven |
| 6,896,673 B2 | 5/2005 | Hooven |

| | | |
|---|---|---|
| 6,899,710 B2 | 5/2005 | Hooven |
| 6,926,712 B2 | 8/2005 | Phan |
| 6,932,812 B2 | 8/2005 | Crowley et al. |
| 6,939,350 B2 | 9/2005 | Phan |
| 6,942,661 B2 | 9/2005 | Swanson |
| 6,949,098 B2 | 9/2005 | Mulier et al. |
| 6,997,925 B2 | 2/2006 | Maguire et al. |
| 7,150,097 B2 | 12/2006 | Sremcich et al. |
| 7,207,988 B2 | 4/2007 | Leckrone |
| 7,250,048 B2 | 7/2007 | Francischelli et al. |
| 7,288,088 B2 * | 10/2007 | Swanson ................. 606/20 |
| 7,303,558 B2 | 12/2007 | Swanson |
| 7,326,206 B2 | 2/2008 | Paul et al. |
| 7,347,858 B2 | 3/2008 | Francischelli et al. |
| 7,371,233 B2 | 5/2008 | Swanson et al. |
| 2002/0002372 A1 | 1/2002 | Jahns et al. |
| 2002/0016588 A1 | 2/2002 | Wong et al. |
| 2002/0026187 A1 | 2/2002 | Swanson |
| 2002/0058934 A1 | 5/2002 | Wang et al. |
| 2002/0103484 A1 | 8/2002 | Hooven |
| 2003/0014048 A1 | 1/2003 | Swanson |
| 2003/0059325 A1 | 3/2003 | Adams |
| 2003/0069572 A1 | 4/2003 | Wellman et al. |
| 2003/0120268 A1 | 6/2003 | Bertolero et al. |
| 2003/0139644 A1 | 7/2003 | Parsons et al. |
| 2003/0144656 A1 | 7/2003 | Ocel et al. |
| 2004/0059324 A1 | 3/2004 | Francischelli et al. |
| 2004/0059325 A1 | 3/2004 | Swanson |
| 2004/0087935 A1 | 5/2004 | Taimisto |
| 2004/0186467 A1 | 9/2004 | Swanson |
| 2005/0019545 A1 | 1/2005 | Riebel |
| 2005/0113827 A1 * | 5/2005 | Dumbauld et al. ............ 606/45 |
| 2005/0119648 A1 | 6/2005 | Swanson |
| 2005/0119649 A1 | 6/2005 | Swanson |
| 2005/0119653 A1 | 6/2005 | Swanson |
| 2005/0119654 A1 | 6/2005 | Swanson |
| 2005/0187544 A1 | 8/2005 | Swanson |
| 2005/0215993 A1 | 9/2005 | Phan |
| 2006/0155272 A1 | 7/2006 | Swanson |
| 2006/0155273 A1 | 7/2006 | Swanson |
| 2006/0155274 A1 | 7/2006 | Swanson |
| 2006/0271034 A1 | 11/2006 | Swanson |
| 2007/0198041 A1 | 8/2007 | Rupp et al. |

FOREIGN PATENT DOCUMENTS

| | | |
|---|---|---|
| EP | 0484671 A2 | 9/1991 |
| EP | 0490301 A1 | 6/1992 |
| EP | 0584787 A1 | 3/1994 |
| EP | 0853922 A1 | 7/1998 |
| EP | 0856291 A2 | 8/1998 |
| EP | 1125549 A2 | 8/2001 |
| JP | 2001515751 | 9/2001 |
| JP | 2001522622 | 11/2001 |
| SU | 1253633 A1 | 8/1986 |
| WO | WO 99/12488 A1 | 3/1999 |
| WO | WO 00/24330 A1 | 5/2000 |
| WO | WO 00/29062 A1 | 5/2000 |
| WO | WO 00/42922 A1 | 7/2000 |
| WO | WO 01/72231 A2 | 10/2001 |
| WO | WO 01/80724 A2 | 11/2001 |
| WO | WO 03/070114 A1 | 8/2003 |

OTHER PUBLICATIONS

Office Action dated Apr. 2, 2003 for U.S. Appl. No. 10/080,378, filed Feb. 19, 2002, Inventor: Huy D. Phan (12 pages).
Amendment dated Sep. 11, 2003 for U.S. Appl. No. 10/080,378, filed Feb. 19, 2002, Inventor: Huy D. Phan (12 pages).
Notice of Allowance dated Apr. 6, 2004 for U.S. Appl. No. 10/080,378, filed Feb. 19, 2002, Inventor: Huy D. Phan (6 pages).
Request for Continued Examination dated May 11, 2004 for U.S. Appl. No. 10/080,378, filed Feb. 19, 2002, Inventor: Huy D. Phan (2 pages).
Notice of Allowance dated Mar. 28, 2005 for U.S. Appl. No. 10/080,378, filed Feb. 19, 2002, Inventor: Huy D. Phan (9 pages).
Office Action dated Mar. 5, 2003 for U.S. Appl. No. 10/079,944, filed Feb. 19, 2002, Inventor: Huy D. Phan (10 pages).
Amendment dated Jul. 14, 2003 for U.S. Appl. No. 10/079,944, filed Feb. 19, 2002, Inventor: Huy D. Phan (18 pages).
Office Action dated Oct. 8, 2003 for U.S. Appl. No. 10/079,944, filed Feb. 19, 2002, Inventor: Huy D. Phan (7 pages).
Amendment dated Jan. 12, 2004 for U.S. Appl. No. 10/079,944, filed Feb. 19, 2002, Inventor: Huy D. Phan (13 pages).
Advisory Action dated Feb. 3, 2004 for U.S. Appl. No. 10/079,944, filed Feb. 19, 2002, Inventor: Huy D. Phan (3 pages).
Office Action dated Mar. 4, 2004 for U.S. Appl. No. 10/079,944, filed Feb. 19, 2002, Inventor: Huy D. Phan (6 pages).
Amendment dated May 14, 2004 for U.S. Appl. No. 10/079,944, filed Feb. 19, 2002, Inventor: Huy D. Phan (12 pages).
Office Action dated Oct. 4, 2004 for U.S. Appl. No. 10/079,944, filed Feb. 19, 2002, Inventor: Huy D. Phan (13 pages).
Amendment dated Dec. 9, 2004 for U.S. Appl. No. 10/079,944, filed Feb. 19, 2002, Inventor: Huy D. Phan (5 pages).
Notice of Allowance dated Jan. 18, 2005 for U.S. Appl. No. 10/079,944, filed Feb. 19, 2002, Inventor: Huy D. Phan (7 pages).
Office Action dated Jul. 29, 2005 for U.S. Appl. No. 11/131,671, filed May 17, 2005, Inventor: Huy D. Phan (5 pages).
Response dated Sep. 3, 2005 for U.S. Appl. No. 11/131,671, filed May 17, 2005, Inventor: Huy D. Phan (4 pages).
Office Action dated Sep. 26, 2005 for U.S. Appl. No. 11/131,671, filed May 17, 2005, Inventor: Huy D. Phan 917 pages).
Amendment dated Dec. 2, 2005 for U.S. Appl. No. 11/131,671, filed May 17, 2005, Inventor: Huy D. Phan (14 pages).
Office Action dated Feb. 27, 2006 for U.S. Appl. No. 11/131,671, filed May 17, 2005, Inventor: Huy D. Phan (11 pages).
Amendment dated May 4, 2006 for U.S. Appl. No. 11/131,671, filed May 17, 2005, Inventor: Huy D. Phan (13 pages).
Advisory Action dated May 24, 2006 for U.S. Appl. No. 11/131,671, filed May 17, 2005, Inventor: Huy D. Phan (3 pages).
Office Action dated Jun. 30, 2006 for U.S. Appl. No. 11/131,671, filed May 17, 2005, Inventor: Huy D. Phan (15 pages).
Amendment dated Oct. 28, 2006 for U.S. Appl. No. 11/131,671, filed May 17, 2005, Inventor: Huy D. Phan (10 pages).
Office Action dated Jan. 17, 2007 for U.S. Appl. No. 11/131,671, filed May 17, 2005, Inventor: Huy D. Phan (4 pages).
Amendment dated Feb. 14, 2007 for U.S. Appl. No. 11/131,671, filed May 17, 2005, Inventor: Huy D. Phan (11 pages).
Terminal Disclaimer dated Apr. 27, 2007 for U.S. Appl. No. 11/131,671, filed May 17, 2005, Inventor: Huy D. Phan (16 pages).
Notice of Allowance dated May 10, 2007 for U.S. Appl. No. 11/131,671, filed May 17, 2005, Inventor: Huy D. Phan (8 pages).
Notice of Allowance dated Aug. 22, 2007 for U.S. Appl. No. 11/131,671, filed May 17, 2005, Inventor: Huy D. Phan (6 pages).
Notice of Allowance dated Jan. 9, 2008 for U.S. Appl. No. 11/131,671, filed May 17, 2005, Inventor: Huy D. Phan (5 pages).
Request for Continued Examination dated Apr. 3, 2008, for U.S. Appl. No. 11/131,671, filed May 17, 2005, Inventor: Huy D. Phan (2 pages).
Notice of Allowance dated Apr. 16, 2008 for U.S. Appl. No. 11/131,671, filed May 17, 2005, Inventor: Huy D. Phan (5 pages).
Office Action dated Mar. 4, 2003 for U.S. Appl. No. 10/080,374, filed Feb. 19, 2002, Inventor: David K. Swanson (14 pages).
Amendment dated Jul. 14, 2003 for U.S. Appl. No. 10/080,374, filed Feb. 19, 2002, Inventor: David K. Swanson (17 pages).
Office Action dated Oct. 9, 2003 for U.S. Appl. No. 10/080,374, filed Feb. 19, 2002, Inventor: David K. Swanson (8 pages).
Amendment dated Jan. 15, 2004 for U.S. Appl. No. 10/080,374, filed Feb. 19, 2002, Inventor: David K. Swanson (13 pages).
Advisory Action dated Feb. 3, 2004 for U.S. Appl. No. 10/080,374, filed Feb. 19, 2002, Inventor: David K. Swanson (2 pages).
Office Action dated Mar. 24, 2004 for U.S. Appl. No. 10/080,374, filed Feb. 19, 2002, Inventor: David K. Swanson (10 pages).
Amendment dated May 24, 2004 for U.S. Appl. No. 10/080,374, filed Feb. 19, 2002, Inventor: David K. Swanson (18 pages).
Office Action dated Sep. 30, 2004 for U.S. Appl. No. 10/080,374, filed Feb. 19, 2002, Inventor: David K. Swanson (9 pages).

Amendment dated Dec. 7, 2004 for U.S. Appl. No. 10/080,374, filed Feb. 19, 2002, Inventor: David K. Swanson (15 pages).
Advisory Action dated Jan. 3, 2005 for U.S. Appl. No. 10/080,374, filed Feb. 19, 2002, Inventor: David K. Swanson (2 pages).
Office Action dated Feb. 14, 2005 for U.S. Appl. No. 10/080,374, filed Feb. 19, 2002, Inventor: David K. Swanson (7 pages).
Amendment dated Mar. 8, 2005 for U.S. Appl. No. 10/080,374, filed Feb. 19, 2002, Inventor: David K. Swanson (8 pages).
Office Action dated Mar. 30, 2005 for U.S. Appl. No. 10/080,374, filed Feb. 19, 2002, Inventor: David K. Swanson (2 pages).
Response dated Apr. 2, 2005 for U.S. Appl. No. 10/080,374, filed Feb. 19, 2002, Inventor: David K. Swanson (7 pages).
Office Action dated May 18, 2005 for U.S. Appl. No. 10/080,374, filed Feb. 19, 2002, Inventor: David K. Swanson (7 pages).
Amendment dated Oct. 17, 2005 for U.S. Appl. No. 10/080,374, filed Feb. 19, 2002, Inventor: David K. Swanson (15 pages).
Office Action dated Jan. 9, 2006 for U.S. Appl. No. 10/080,374, filed Feb. 19, 2002, Inventor: David K. Swanson (10 pages).
Amendment dated Apr. 12, 2006 for U.S. Appl. No. 10/080,374, filed Feb. 19, 2002, Inventor: David K. Swanson (17 pages).
Advisory Action dated Apr. 24, 2006 for U.S. Appl. No. 10/080,374, filed Feb. 19, 2002, Inventor: David K. Swanson (3 pages).
Office Action dated Jun. 14, 2006 for U.S. Appl. No. 10/080,374, filed Feb. 19, 2002, Inventor: David K. Swanson (8 pages).
Amendment dated Oct. 28, 2006 for U.S. Appl. No. 10/080,374, filed Feb. 19, 2002, Inventor: David K. Swanson (11 pages).
Office Action dated Jan. 9, 2007 for U.S. Appl. No. 10/080,374, filed Feb. 19, 2002, Inventor: David K. Swanson (9 pages).
Amendment dated Mar. 9, 2007 for U.S. Appl. No. 10/080,374, filed Feb. 19, 2002, Inventor: David K. Swanson (11 pages).
Advisory Action dated Mar. 21, 2007 for U.S. Appl. No. 10/080,374, filed Feb. 19, 2002, Inventor: David K. Swanson (3 pages).
Office Action dated Apr. 19, 2007 for U.S. Appl. No. 10/080,374, filed Feb. 19, 2002, Inventor: David K. Swanson (12 pages).
Amendment dated Jul. 19, 2007 for U.S. Appl. No. 10/080,374, filed Feb. 19, 2002, Inventor: David K. Swanson (12 pages).
Office Action dated Oct. 9, 2007 for U.S. Appl. No. 10/080,374, filed Feb. 19, 2002, Inventor: David K. Swanson (13 pages).
Amendment and Request for Continued Examination dated Oct. 31, 2007 for U.S. Appl. No. 10/080,374, filed Feb. 19, 2002, Inventor: David K. Swanson (22 pages).
Office Action dated Jan. 9, 2008 for U.S. Appl. No. 10/080,374, filed Feb. 19, 2002, Inventor: David K. Swanson (6 pages).
Response dated Feb. 6, 2008 for U.S. Appl. No. 10/080,374, filed Feb. 19, 2002, Inventor: David K. Swanson (6 pages).
Office Action dated Apr. 16, 2008 for U.S. Appl. No. 10/080,374, filed Feb. 19, 2002, Inventor: David K. Swanson (7 pages).
Office Action dated Mar. 3, 2003 for U.S. Appl. No. 10/079,948, filed Feb. 19, 2002, Inventor: David K. Swanson (8 pages).
Amendment dated Jul. 15, 2003 for U.S. Appl. No. 10/079,948, filed Feb. 19, 2002, Inventor: David K. Swanson (19 pages).
Office Action dated Oct. 8, 2003 for U.S. Appl. No. 10/079,948, filed Feb. 19, 2002, Inventor: David K .Swanson (15 pages).
Amendment dated Jan. 15, 2004 for U.S. Appl. No. 10/079,948, filed Feb. 19, 2002, Inventor: David K. Swanson (17 pages).
Advisory Action dated Feb. 3, 2004 for U.S. Appl. No. 10/079,948, filed Feb. 19, 2002, Inventor: David K. Swanson (3 pages).
Request for Continued Examination dated Feb. 8, 2004 for U.S. Appl. No. 10/079,948, filed Feb. 19, 2002, Inventor: David K. Swanson (2 pages).
Office Action dated Mar. 26, 2004 for U.S. Appl. No. 10/079,948, filed Feb. 19, 2002, Inventor: David K. Swanson (11 pages).
Amendment dated May 24, 2004 for U.S. Appl. No. 10/079,948, filed Feb. 19, 2002, Inventor: David K. Swanson (20 pages).
Office Action dated Oct. 4, 2004 for U.S. Appl. No. 10/079,948, filed Feb. 19, 2002, Inventor: David K. Swanson (16 pages).
Amendment dated Dec. 7, 2004 for U.S. Appl. No. 10/079,948, filed Feb. 19, 2002, Inventor: David K. Swanson (23 pages).
Office Action dated Jan. 18, 2005 for U.S. Appl. No. 10/079,948, filed Feb. 19, 2002, Inventor: David K. Swanson (6 pages).
Response dated Feb. 23, 2005 for U.S. Appl. No. 10/079,948, filed Feb. 19, 2002, Inventor: David K. Swanson (3 pages).
Office Action dated May 19, 2005 for U.S. Appl. No. 10/079,948, filed Feb. 19, 2002, Inventor: David K. Swanson (17 pages).
Amendment dated Oct. 17, 2005 for U.S. Appl. No. 10/079,948, filed Feb. 19, 2002, Inventor: David K. Swanson (14 pages).
Office Action dated Jan. 12, 2006 for U.S. Appl. No. 10/079,948, filed Feb. 19, 2002, Inventor: David K. Swanson (14 pages).
Amendment dated Apr. 12, 2006 for U.S. Appl. No. 10/079,948, filed Feb. 19, 2002, Inventor: David K. Swanson (11 pages).
Notice of Allowance dated Jun. 14, 2006 for U.S. Appl. No. 10/079,948, filed Feb. 19, 2002, Inventor: David K. Swanson (8 pages).
Notice of Abandonment dated Oct. 19, 2006 for U.S. Appl. No. 10/079,948, filed Feb. 19, 2002, Inventor: David K. Swanson (2 pages).
Petition under 37 C.F.R. 1.137(b) dated Mar. 15, 2007 for U.S. Appl. No. 10/079,948, filed Feb. 19, 2002, Inventor: David K. Swanson (4 pages).
Decision on Petition under 37 C.F.R. 1.137(b) dated Aug. 16, 2007 for U.S. Appl. No. 10/079,948, filed Feb. 19, 2002, Inventor: David K. Swanson (4 pages).
Renewed Petition under 37 C.F.R. 1.137(b) dated Feb. 29, 2008 for U.S. Appl. No. 10/079,948, filed Feb. 19, 2002, Inventor: David K. Swanson (13 pages).
Office Action dated Aug. 25, 2006 for U.S. Appl. No. 10/727,144, filed Dec. 2, 2003, Inventor: David K. Swanson (26 pages).
Amendment dated Nov. 15, 2006 for U.S. Appl. No. 10/727,144, filed Dec. 2, 2003, Inventor: David K. Swanson (12 pages).
Office Action dated Jan. 31, 2007 for U.S. Appl. No. 10/727,144, filed Dec. 2, 2003, Inventor: David K. Swanson (11 pages).
Amendment dated Apr. 26, 2007 for U.S Appl. No. 10/727,144, filed Dec. 2, 2003, Inventor: David K. Swanson (13 pages).
Office Action dated Jul. 13, 2007 for U.S. Appl. No. 10/727,144, filed Dec. 2, 2003, Inventor: David K. Swanson (9 pages).
Amendment dated Sep. 13, 2007 for U.S. Appl. No. 10/727,144, filed Dec. 2, 2003, Inventor: David K. Swanson (16 pages).
Advisory Action dated Oct. 9, 2007 for U.S. Appl. No. 10/727,144, filed Dec. 2, 2003, Inventor: David K. Swanson (3 pages).
Request for Continued Examination dated Nov. 18, 2007 for U.S. Appl. No. 10/727,144, filed Dec. 2, 2003, Inventor: David K. Swanson (1 page).
Office Action dated Jan. 18, 2008 for U.S. Appl. No. 10/727,144, filed Dec. 2, 2003, Inventor: David K. Swanson (19 pages).
Amendment dated May 19, 2008 for U.S. Appl. No. 10/727,144, filed Dec. 2, 2003, Inventor: David K. Swanson (16 pages).
Office Action dated Mar. 26, 2008 for U.S. Appl. No. 11/031,629, filed Jan. 8, 2005, Inventor: David Swanson (16 pages).
Office Action dated Mar. 25, 2008 for U.S. Appl. No. 11/031,631, filed Jan. 8, 2005, Inventor: David K. Swanson (12 pages).
Office Action dated Mar. 27, 2007 for U.S. Appl. No. 11/067,391, filed Feb. 25, 2005, Inventor: Greg Eberl (5 pages).
Response dated Apr. 16, 2007 for U.S. Appl. No. 11/067,391, filed Feb. 25, 2005, Inventor: Greg Eberl (7 pages).
Office Action dated Jun. 28, 2007 for U.S. Appl. No. 11/067,391, filed Feb. 25, 2005, Inventor: Greg Eberl (12 pages).
Amendment dated Sep. 28, 2007 for U.S. Appl. No. 11/067,391, filed Feb. 25, 2005, Inventor: Greg Eberl (10 pages).
Office Action dated Dec. 28, 2007 for U.S. Appl. No. 11/067,391, filed Feb. 25, 2005, Inventor: Greg Eberl (9 pages).
Amendment dated Mar. 27, 2008 for U.S. Appl. No. 11/067,391, filed Feb. 25, 2005, Inventor: Greg Eberl (11 pages).
Office Action dated Mar. 24, 2008 for U.S. Appl. No. 11/031,630, filed Jan. 8, 2005, Inventor: David K. Swanson (13 pages).
Office Action dated May 28, 2008 for U.S. Appl. No. 11/141,405, filed May 28, 2005, Inventor: David K. Swanson (7 pages).
PCT International Search Report for PCT/US2002/38105, Applicant: Scimed Life Systems, Inc., Form PCT/ISA/210, dated Jul. 17, 2003 (5 pages).
PCT Written Opinion for PCT/US2002/38105, Applicant: Scimed Life Systems, Inc., Forms PCT/IPEA/408, dated Feb. 20, 2004 (5 pages).
PCT International Preliminary Examination Report for PCT/US2002/38105, Applicant: Scimed Life Systems, Inc., Form PCT/IPEA/409, dated May 27, 2004 (5 pages).

PCT International Search Report for PCT/US2002/38092, Applicant: Scimed Life Systems, Inc., Forms PCT/ISA/210 and PCT/ISA/220, dated Mar. 28, 2003 (7 pages).

PCT Written Opinion for PCT/US2002/38092, Applicant: Scimed Life Systems, Inc., Form PCT/IPEA/408, dated Nov. 13, 2003 (5 pages).

PCT International Preliminary Report on Patentability for PCT/US2002/38092, Applicant: Scimed Life Systems, Inc., Forms PCT/IPEA/416 and PCT/IPEA/409, dated Aug. 19, 2003 (7 pages).

PCT International Search Report for PCT/US2002/38924, Applicant: Scimed Life Systems, Inc., Forms PCT/ISA/210 and PCT/ISA/220, dated May 6, 2003 (7 pages).

PCT International Preliminary Examination Report for PCT/US2002/38924, Applicant: Scimed Life Systems, Inc., Form PCT/IPEA/409, dated May 27, 2004 (5 pages).

PCT International Search Report for PCT/US2002/38093, Applicant: Scimed Life Systems, Inc., Form PCT/ISA/210, dated Mar. 28, 2003 (4 pages).

PCT International Preliminary Examination Report for PCT/US2002/38093, Applicant: Scimed Life Systems, Inc., Form PCT/IPEA/409, dated Mar. 12, 2004 (6 pages).

PCT International Search Report for PCT/US2004/039364, Applicant: Scimed Life Systems, Inc., Form PCT/ISA/210, dated Apr. 12, 2005 (4 pages).

PCT Written Opinion for PCT/US2004/039364, Applicant: Scimed Life Systems, Inc., Form PCT/ISA/237, dated Apr. 12, 2005 (6 pages).

PCT International Preliminary Report on Patentability for PCT/US2004/039364, Applicant: Scimed Life Systems, Inc., Form PCT/IB/373, dated Jun. 7, 2006 (7 pages).

PCT International Search Report for PCT/US2005/045055, Applicant: Boston Scientific Scimed, Inc., Forms PCT/ISA/210 and PCT/ISA/220, dated October 27, 2006 (10 pages).

\* cited by examiner

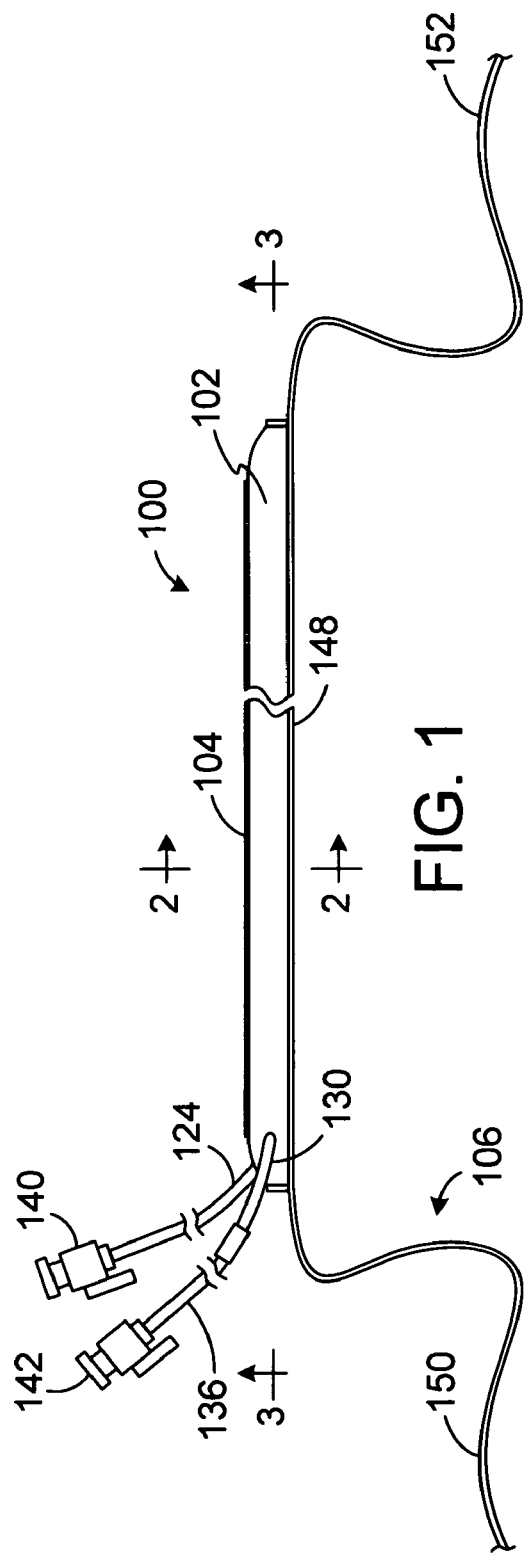
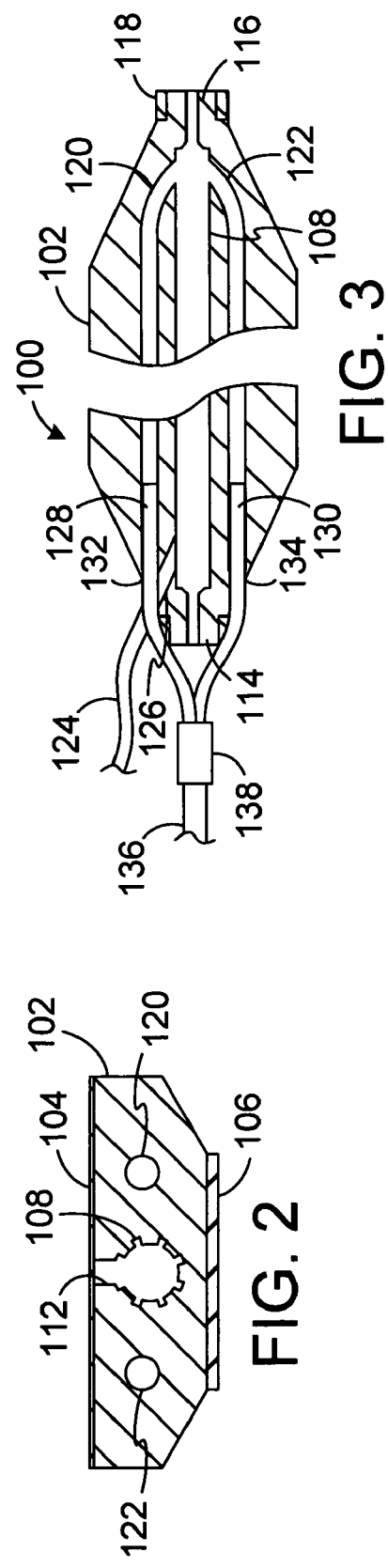

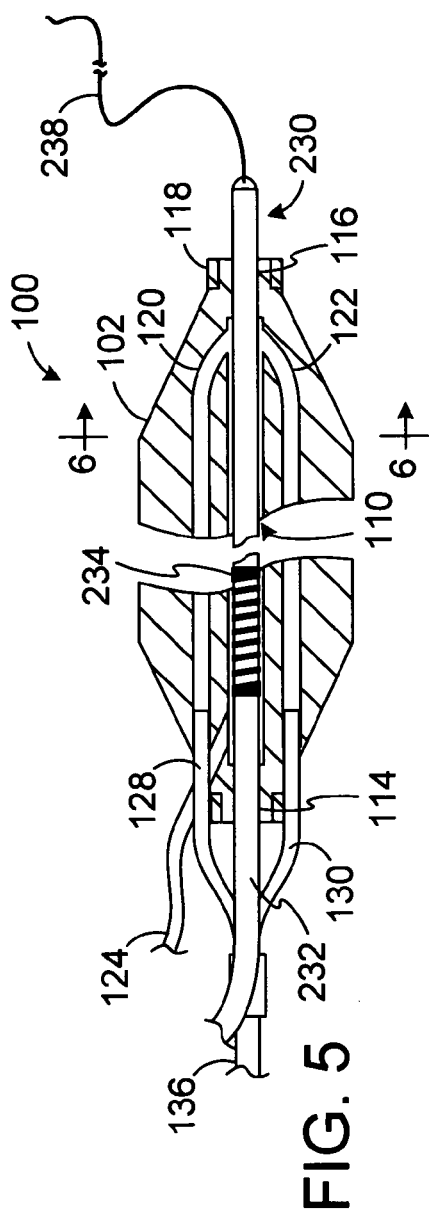
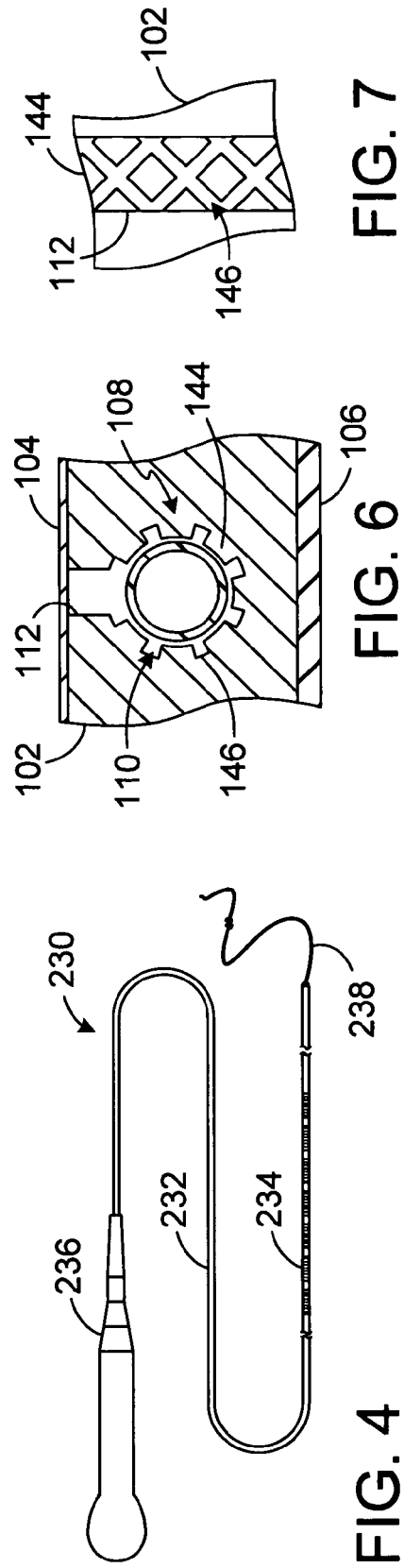
FIG. 5
FIG. 6
FIG. 7
FIG. 4

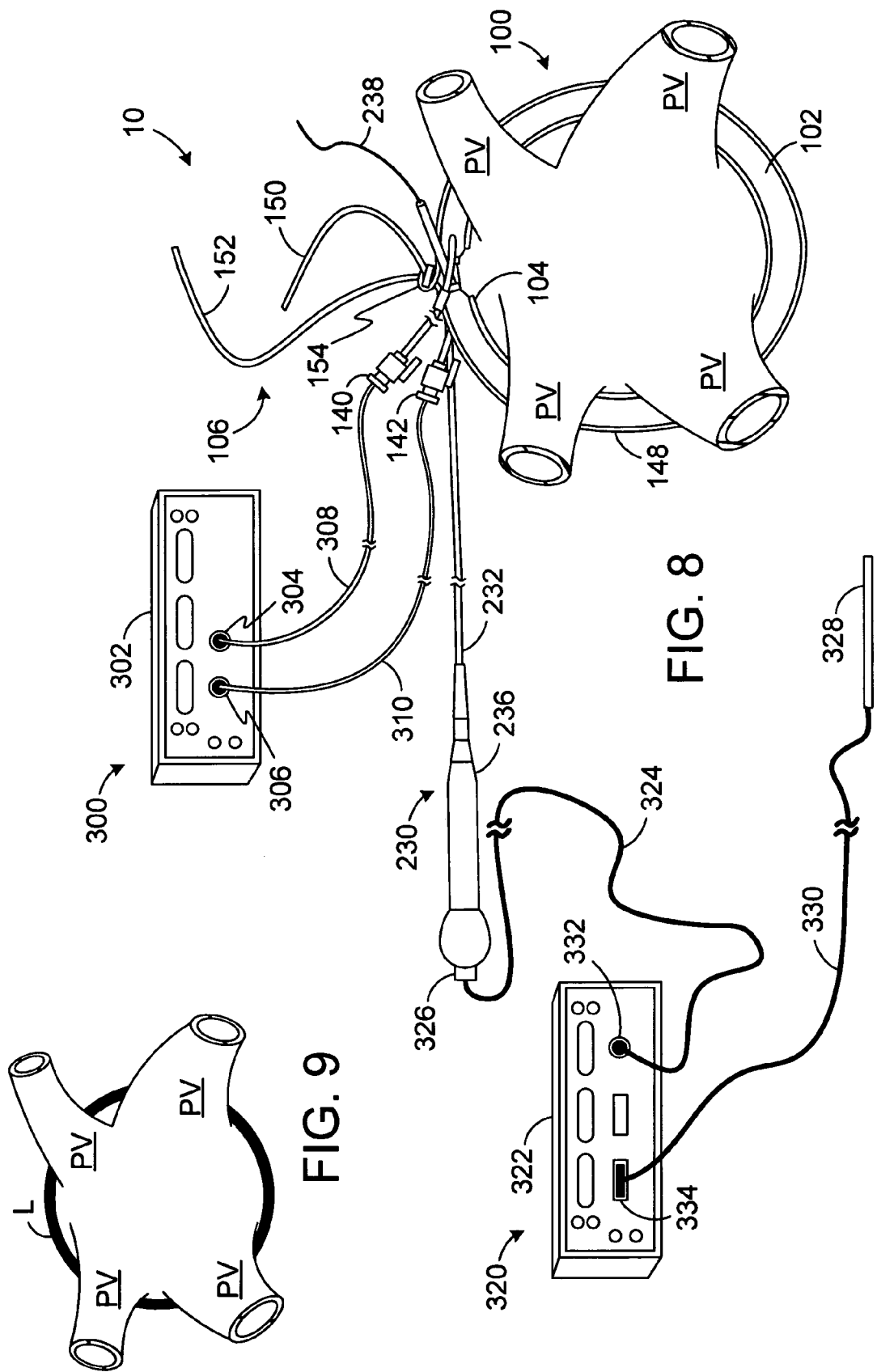

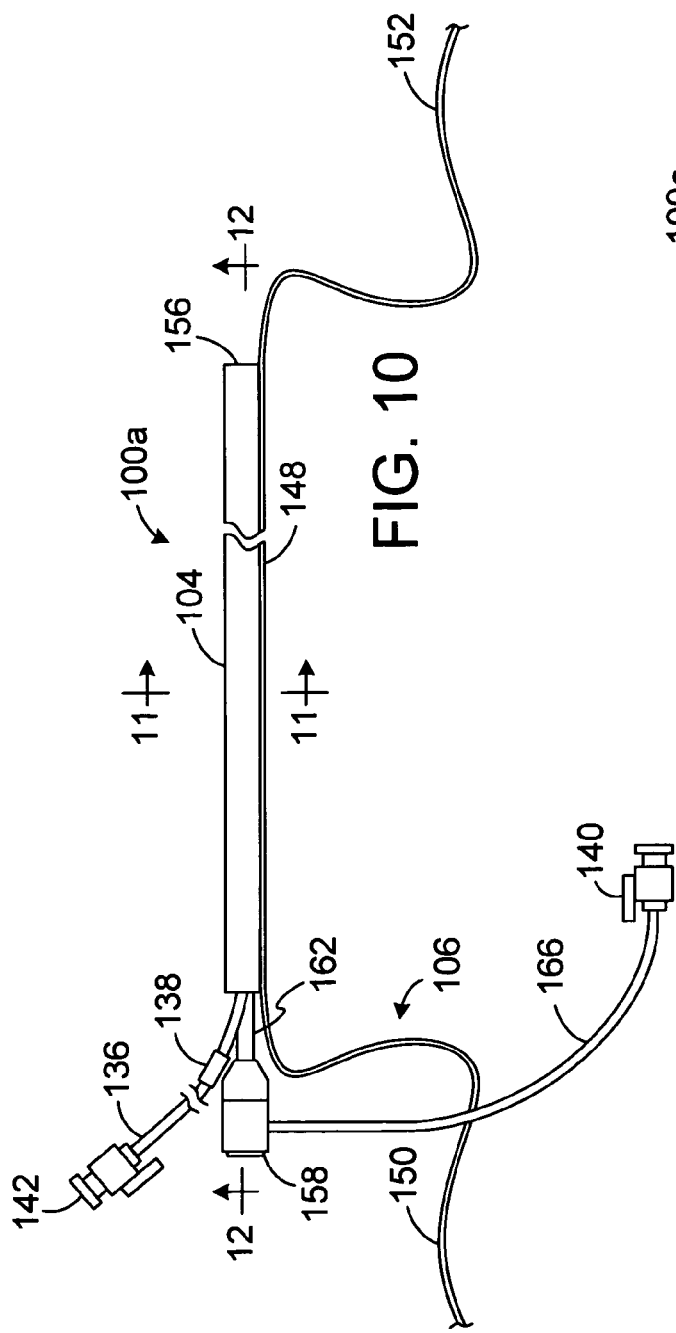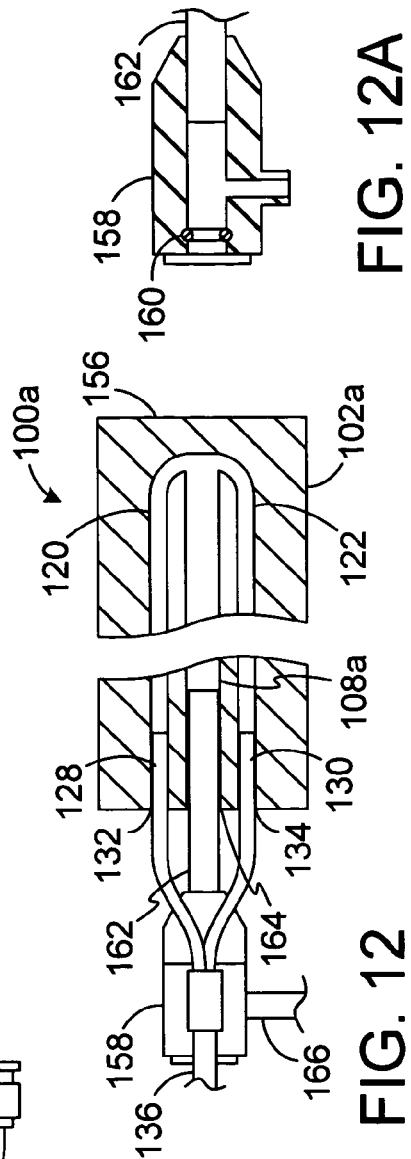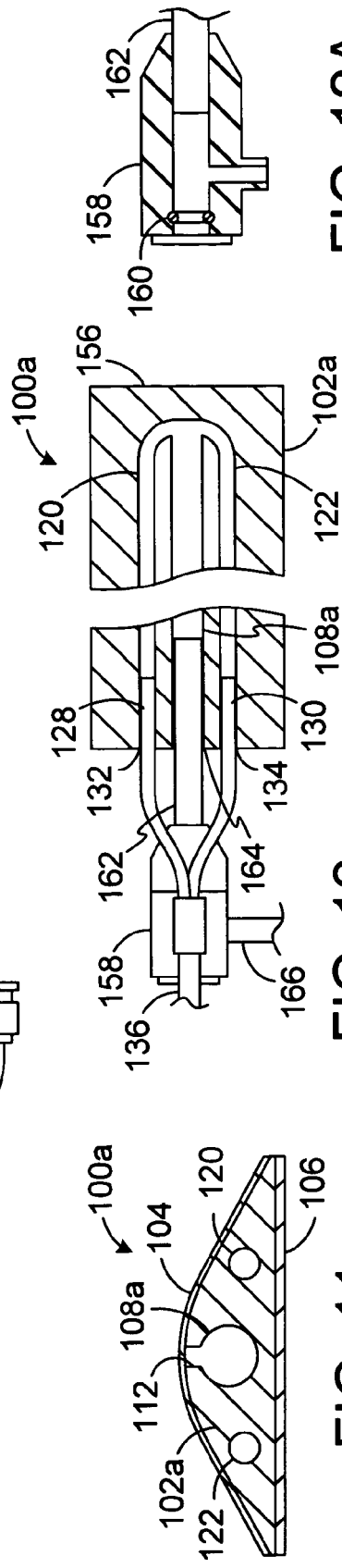

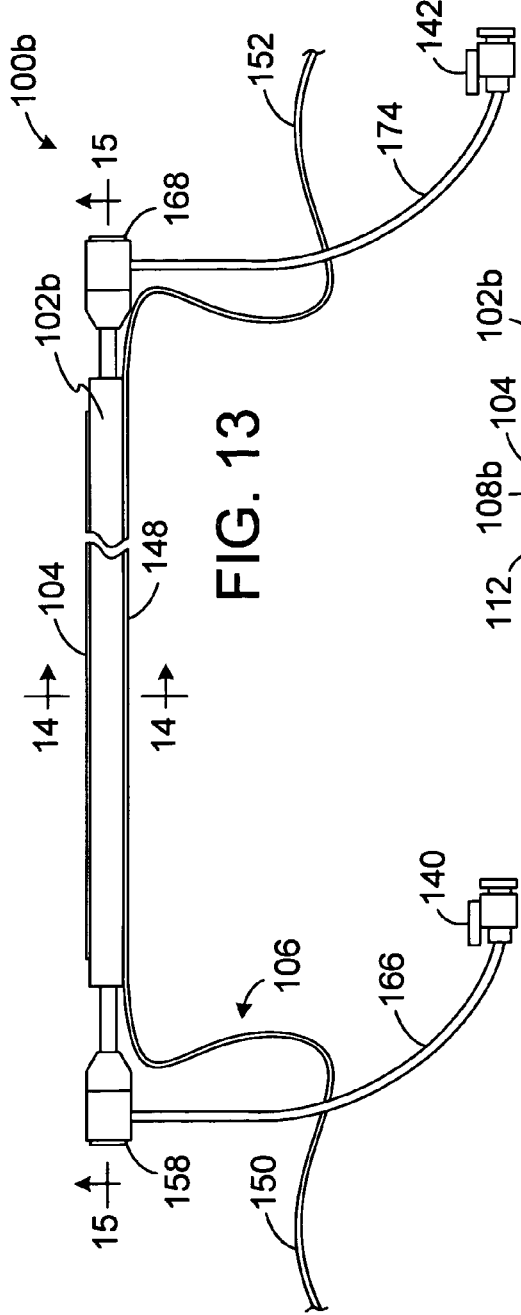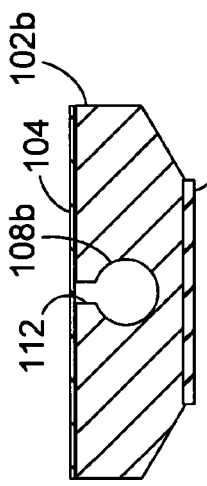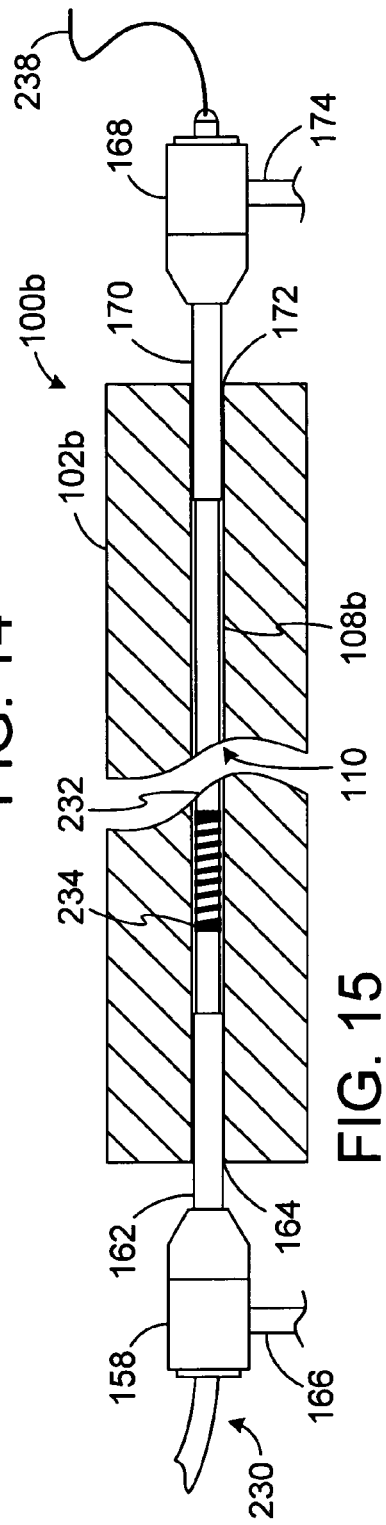

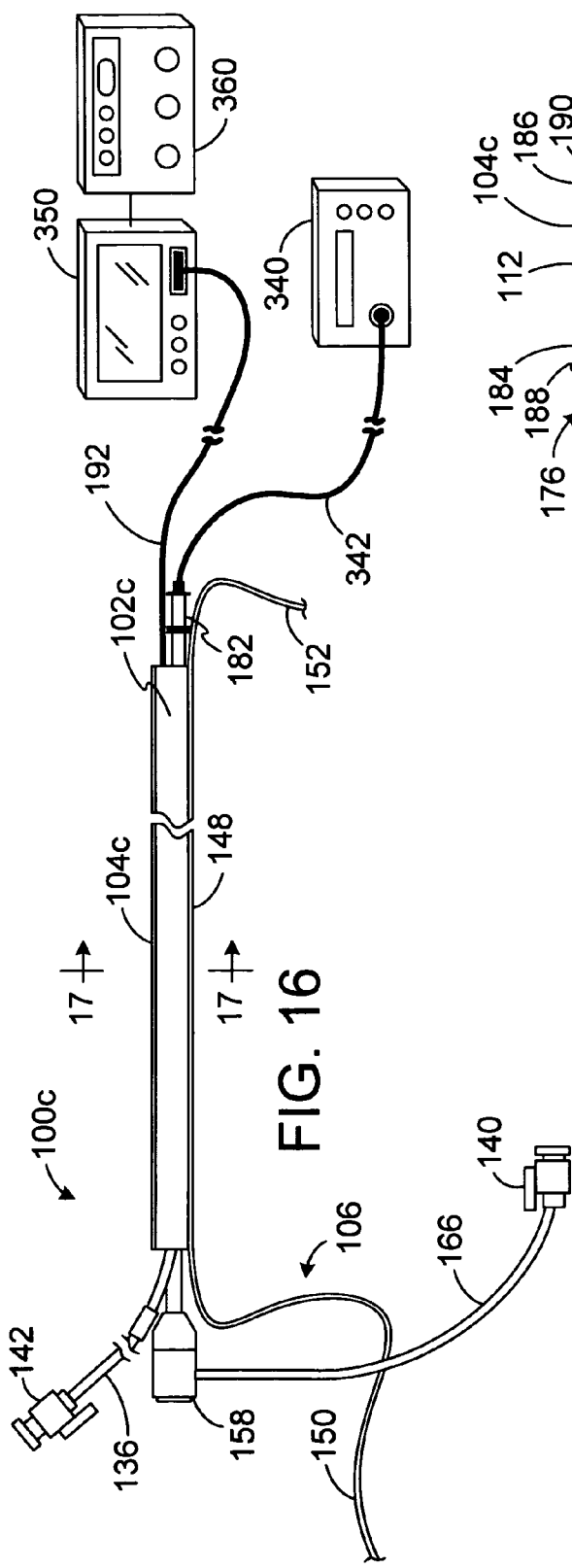
FIG. 16
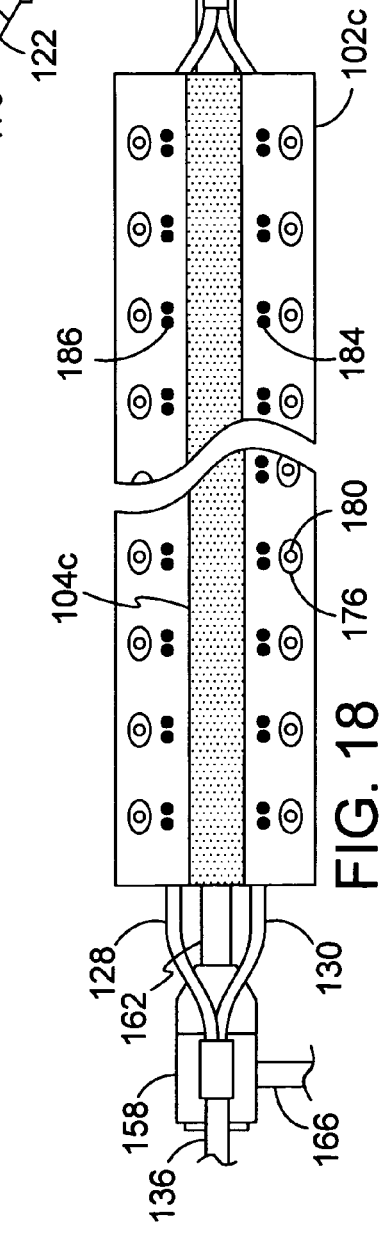
FIG. 17
FIG. 18

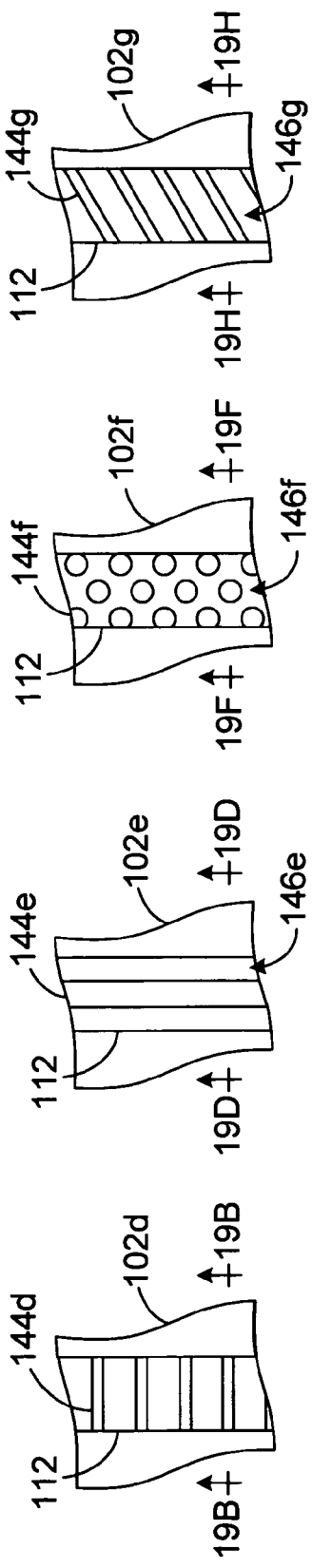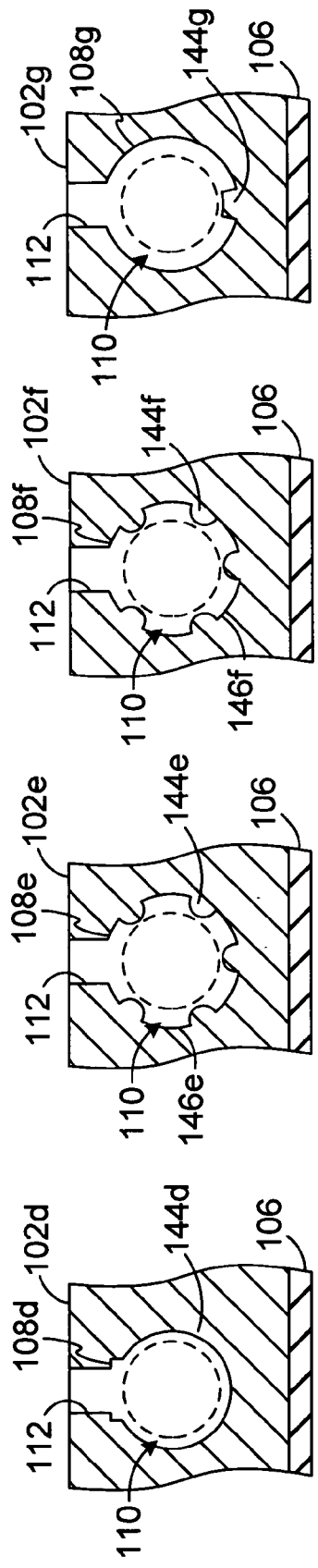

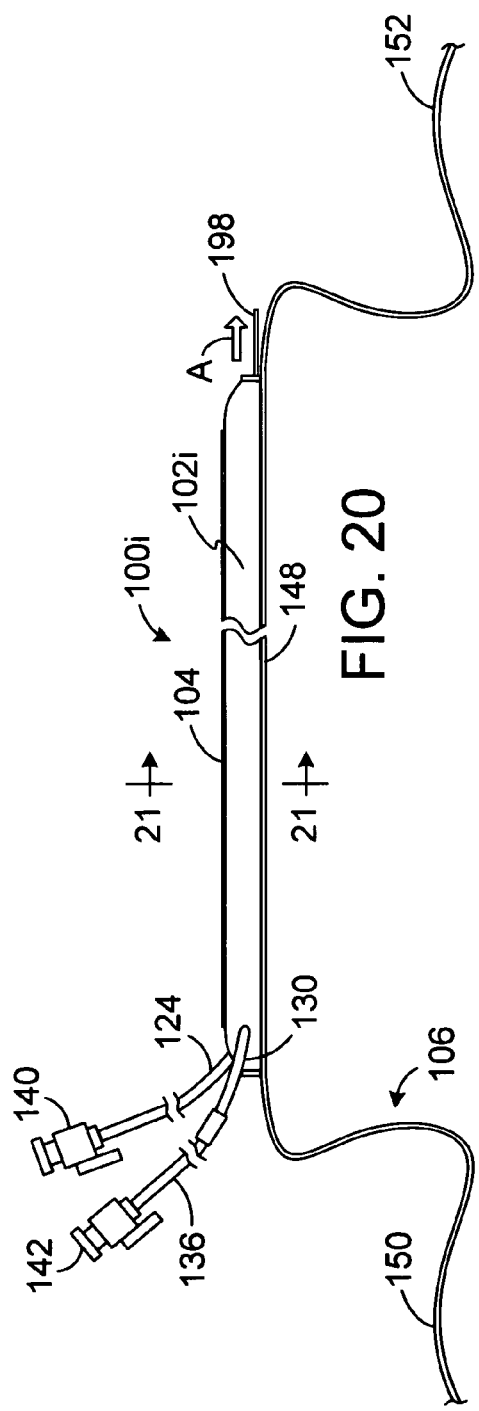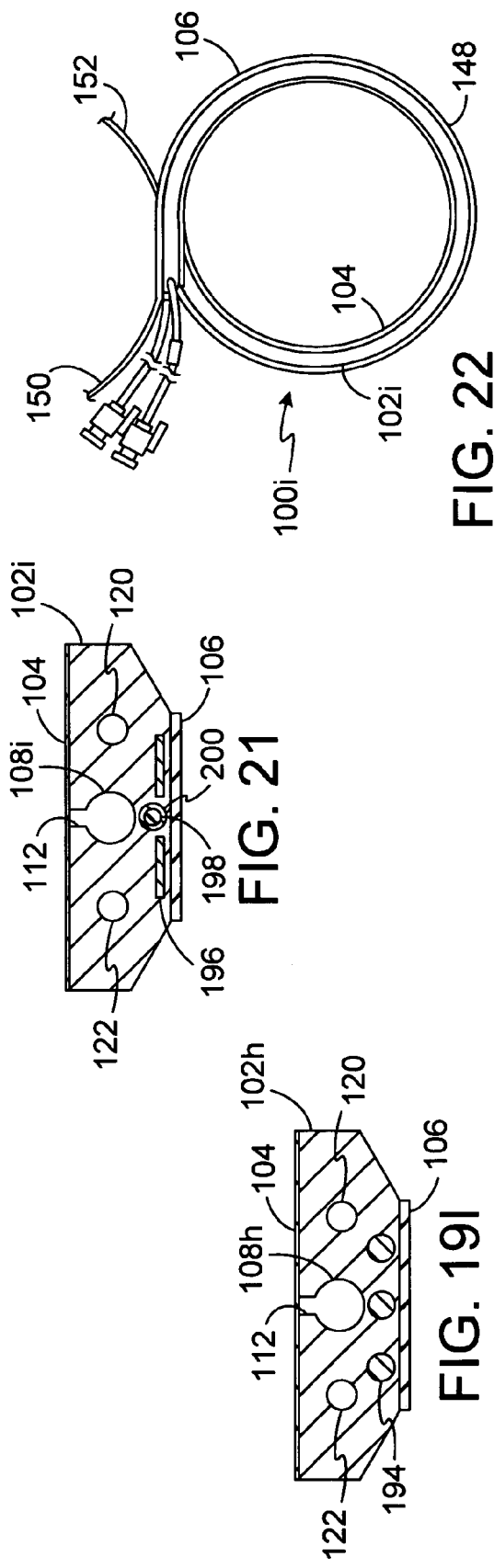

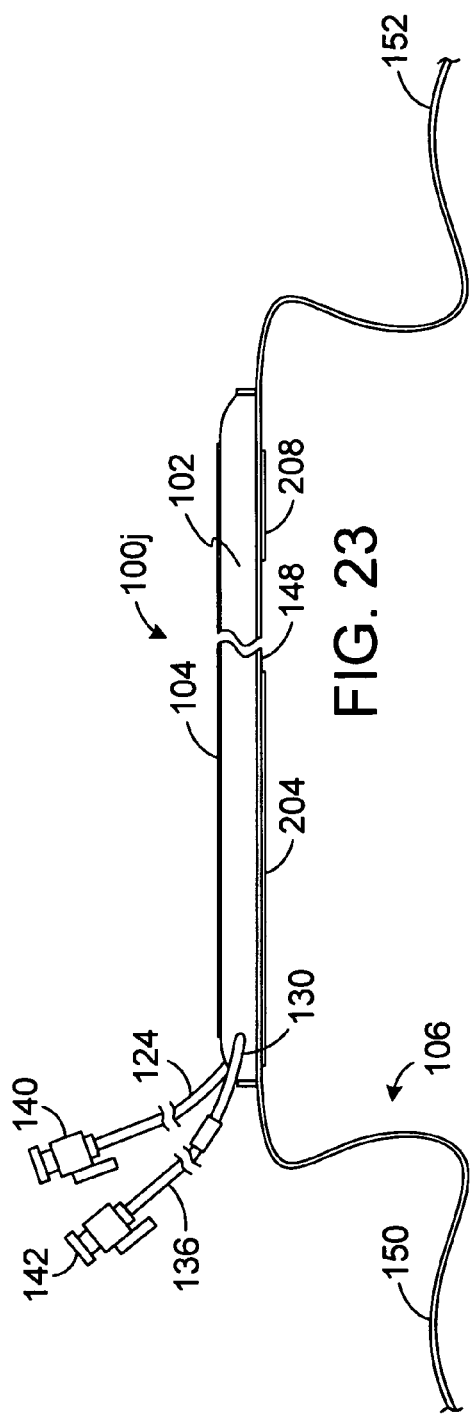
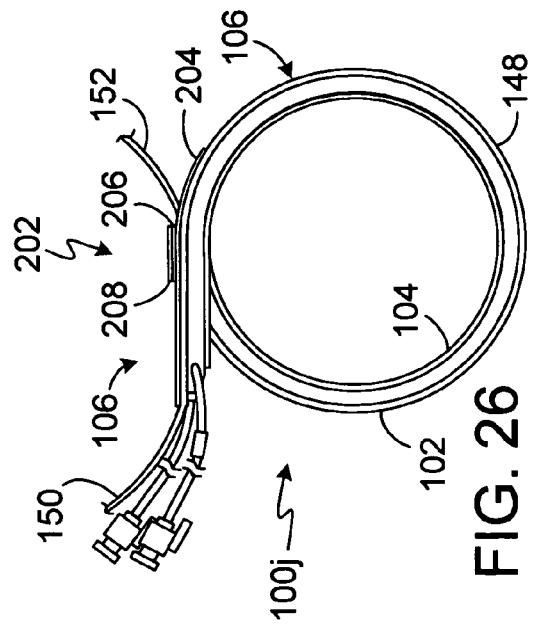
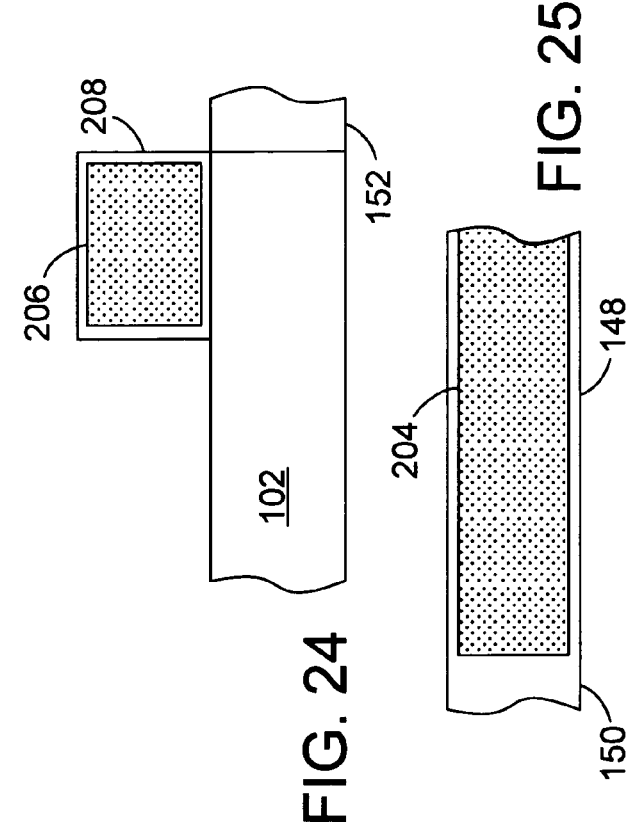
FIG. 23
FIG. 24
FIG. 25
FIG. 26

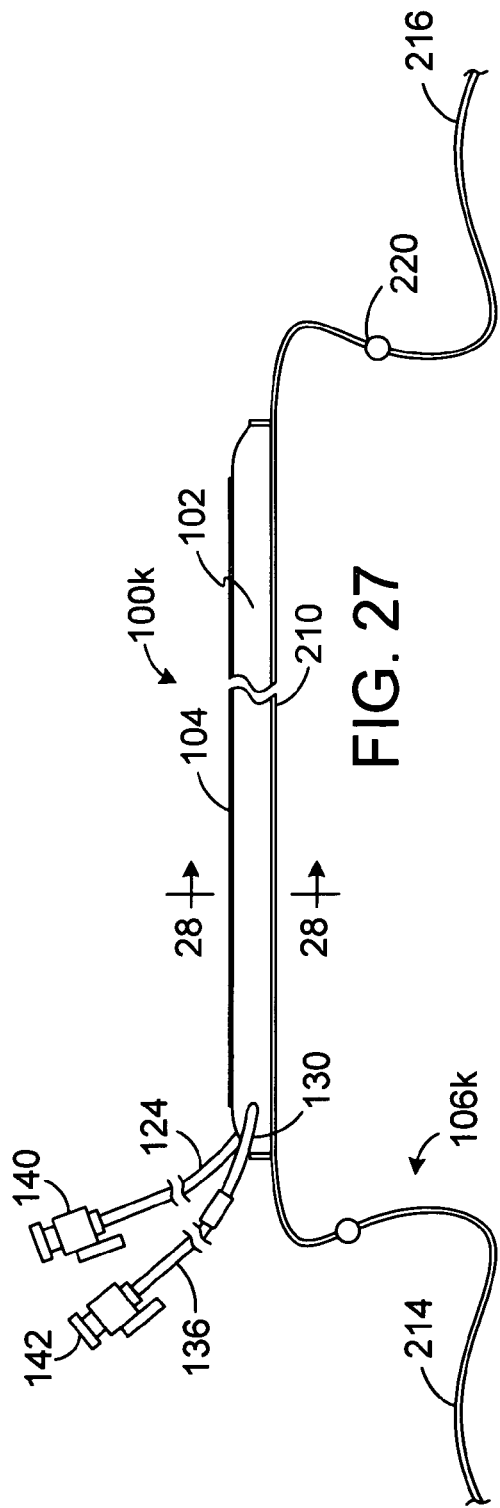
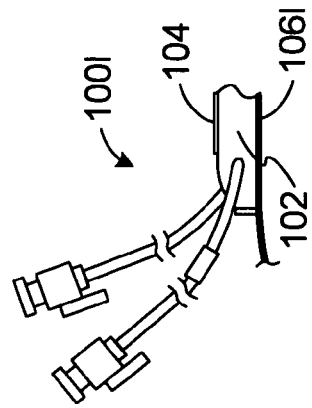
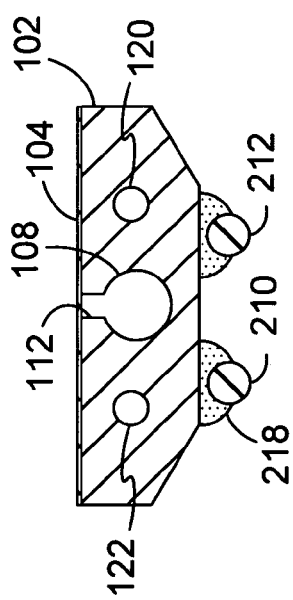

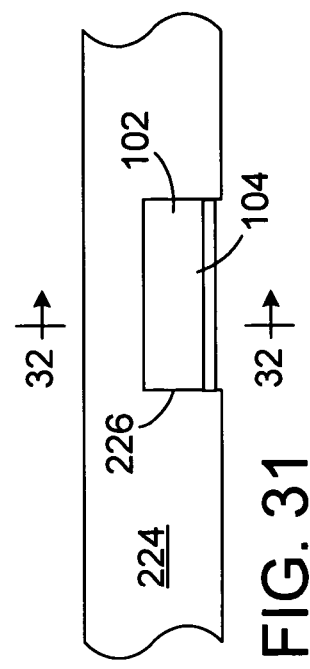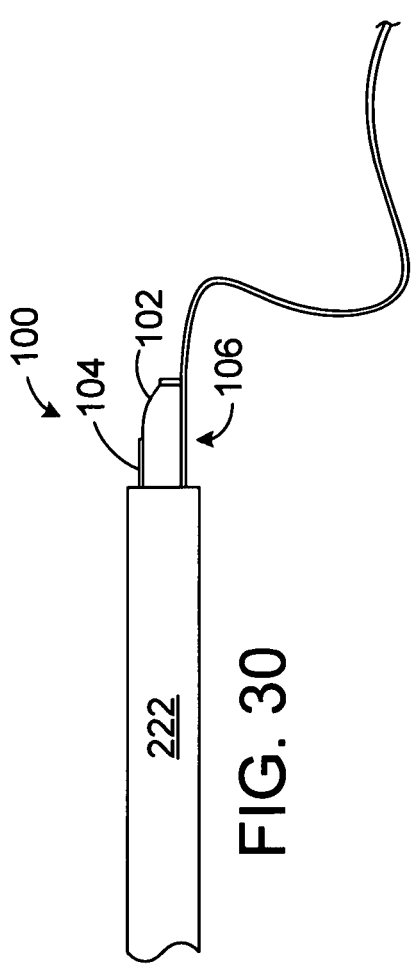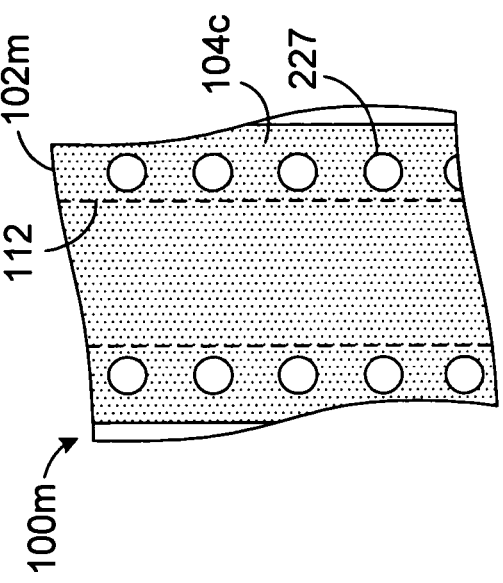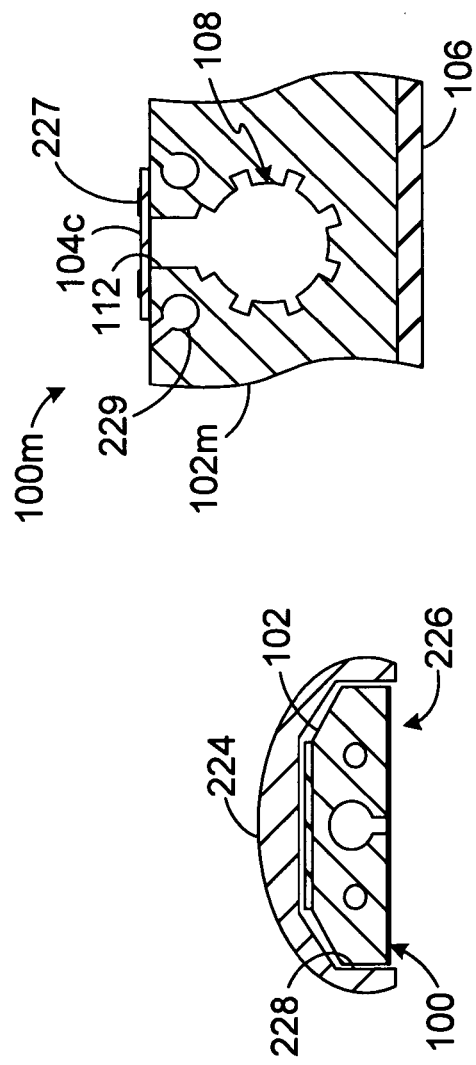

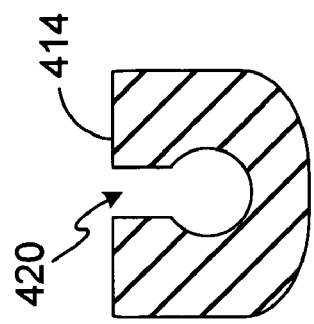
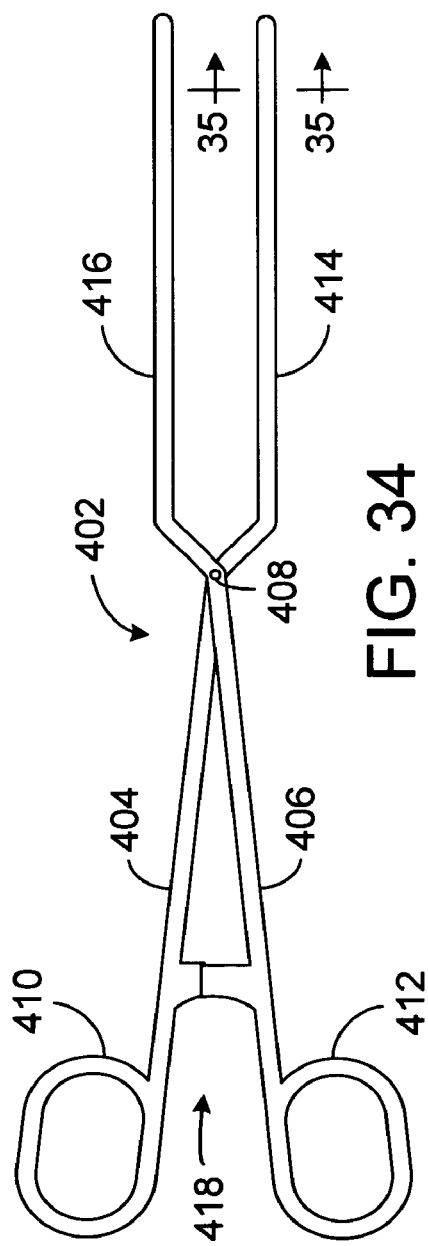
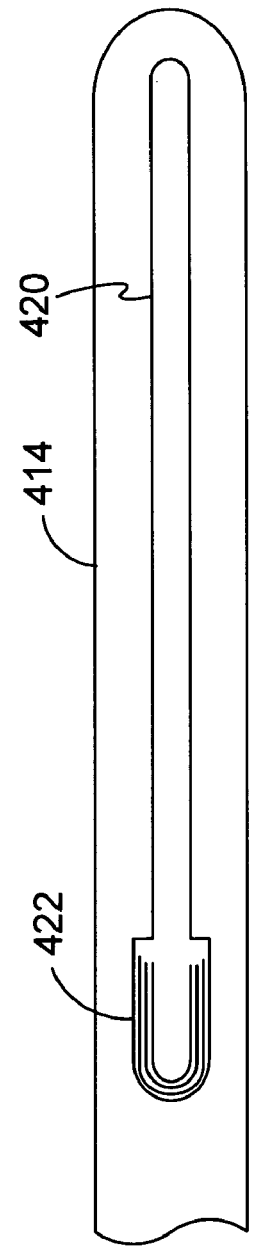

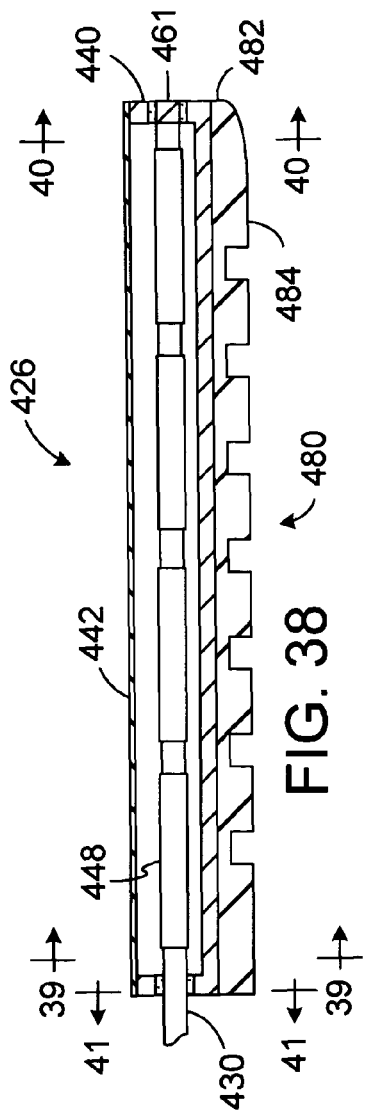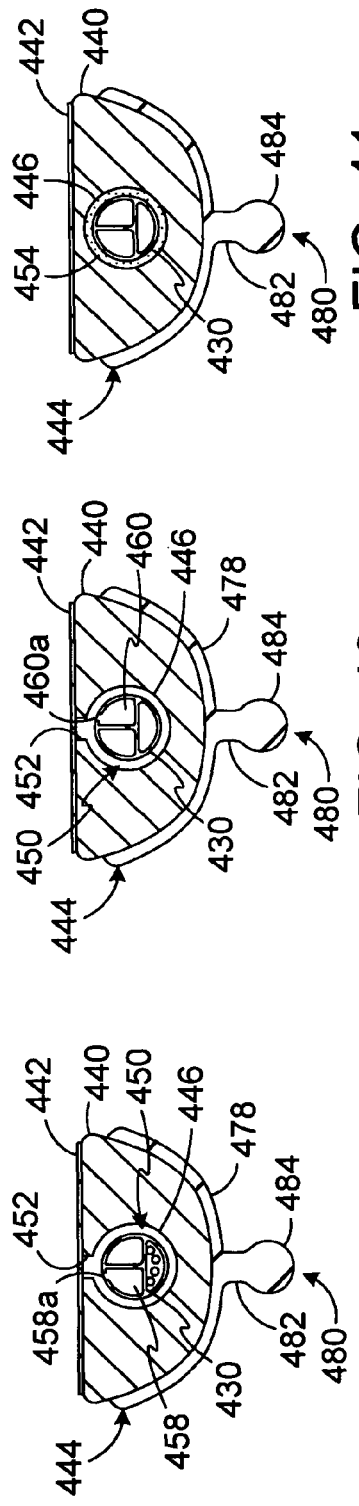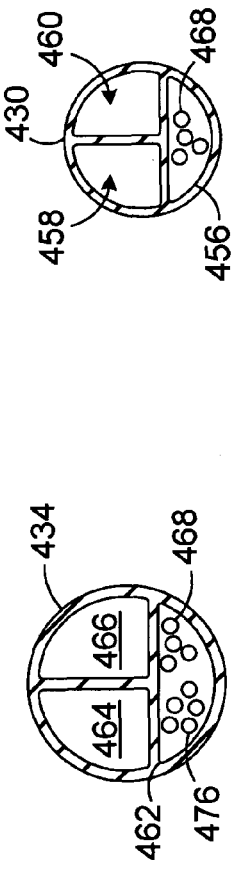

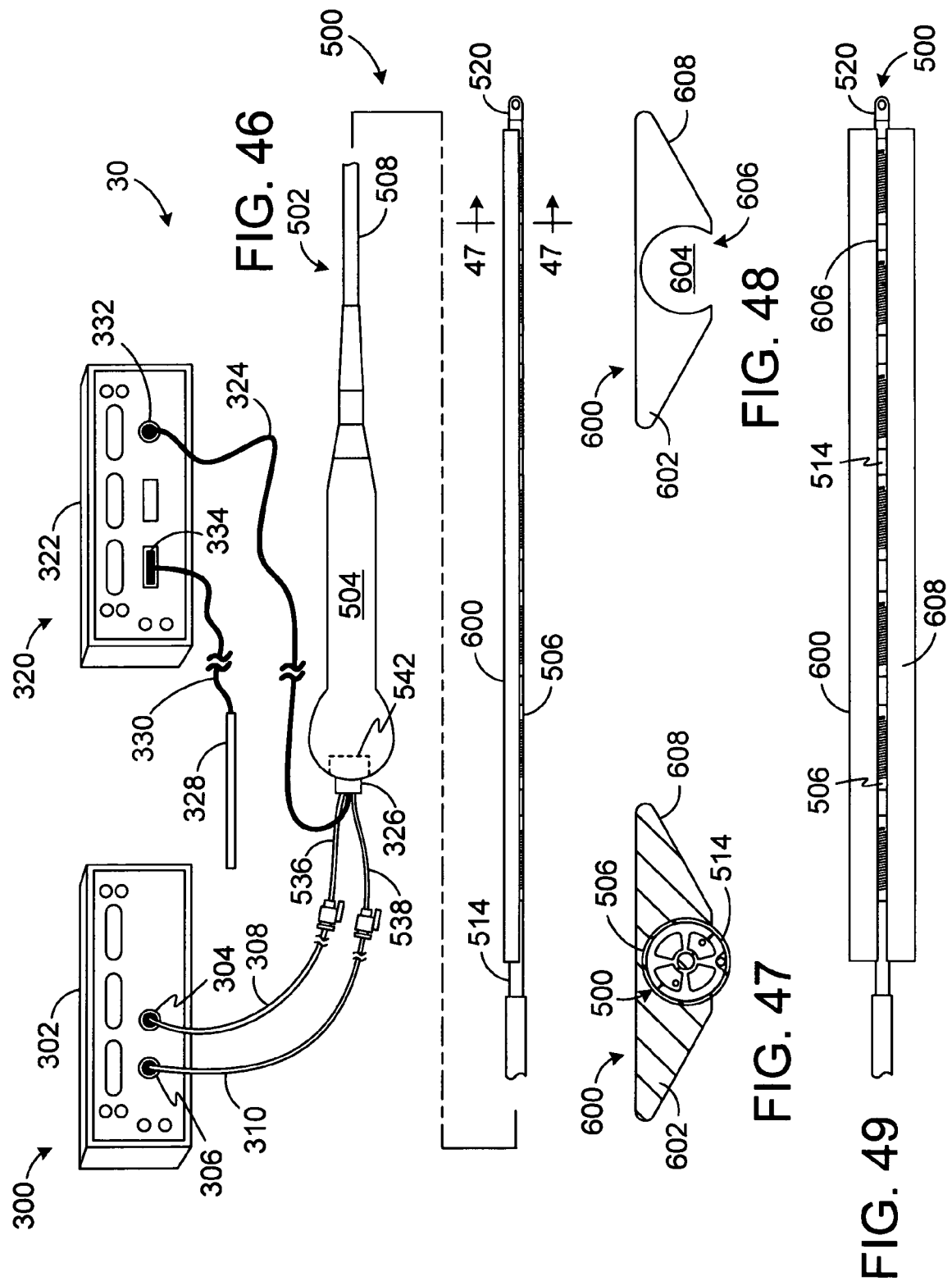

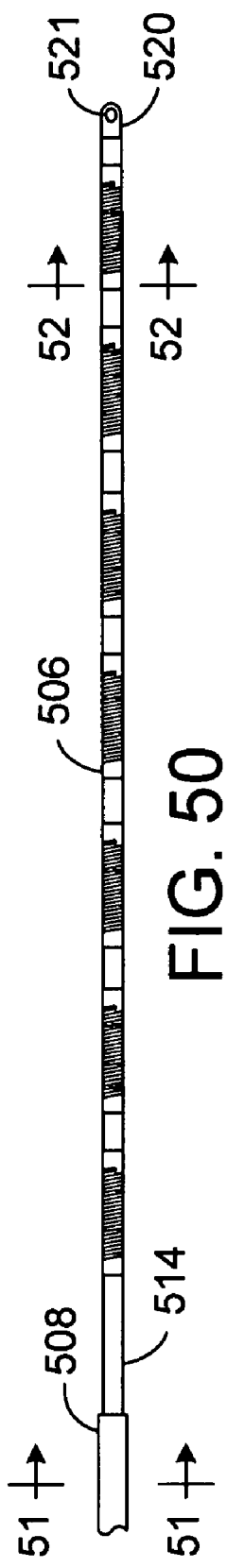
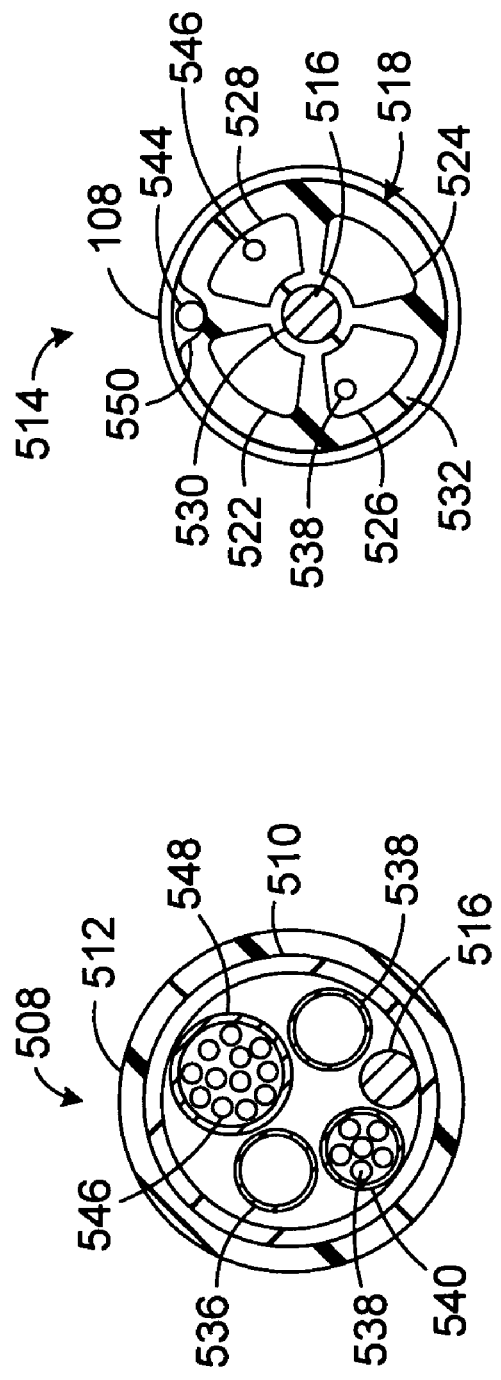
FIG. 50
FIG. 51
FIG. 52

CLAMP BASED LESION FORMATION APPARATUS AND METHODS CONFIGURED TO PROTECT NON-TARGET TISSUE

BACKGROUND OF THE INVENTIONS

1. Field of Inventions

The present inventions relate generally to devices for performing therapeutic operations on body tissue.

2. Description of the Related Art

There are many instances where therapeutic elements must be positioned adjacent to body tissue. One instance involves the formation of therapeutic lesions to treat cardiac conditions such as atrial fibrillation, atrial flutter and arrhythmia. Therapeutic lesions, which may also be used to treat conditions in other regions of the body such as the prostate, liver, brain, gall bladder, uterus, breasts, lungs and other solid organs, are typically formed by ablating tissue.

The present inventor has determined that lesion formation devices are susceptible to improvement. For example, the present inventor has determined that conventional lesion formation devices can be difficult to position and can damage non-target tissue near the tissue in which the therapeutic lesions are being formed. Conventional lesion formation apparatus can also roll in the direction of non-target tissue after being properly positioned. In the context of epicardial pulmonary vein isolation, it is desirable to form lesions in cardiac tissue because ablation of the pulmonary veins or pulmonary vein ostia can lead to stenosis. The present inventor has also determined that it would be desirable to provide devices that more accurately focus tissue coagulation energy during a lesion formation procedure in order to enhance the therapeutic effect, increase efficiency, and reduce the likelihood that non-target tissue will be ablated.

SUMMARY OF THE INVENTIONS

An apparatus in accordance with one invention herein includes an insulation element, defining an exterior surface, a lumen, and a slot that extends from the lumen to the exterior surface such that there are exterior surface portions on opposite sides of the slot and the slot defines a width that is less than the exterior surface portion widths, and an energy transmission element aligned with at least the portion of the slot at the exterior surface of the insulation element.

An apparatus in accordance with another invention herein, which may be carried by, or removably secured to, a clamp member, includes a longitudinally extending insulation element and a longitudinally extending lesion formation region associated with the insulation element such that there are insulation element side portions on opposite sides of the lesion formation region and the side portion widths are greater than the lesion formation region width.

An apparatus in accordance with another invention herein includes a main body and a slot that is configured to receive a probe shaft with one or more energy emission elements. The main body is preferably formed from material that allows it to act as an insulation element.

There are a wide variety of advantages associated with the present inventions. By way of example, but not limitation, and as described in detail below, the present inventions prevent damage to non-target tissue near the target tissue in which the therapeutic lesions are being formed.

BRIEF DESCRIPTION OF THE DRAWINGS

Detailed description of preferred embodiments of the inventions will be made with reference to the accompanying drawings.

FIG. 1 is a side view of an electrophysiology probe positioning wrap in accordance with a preferred embodiment of a present invention.

FIG. 2 is a section view taken along line 2-2 in FIG. 1.

FIG. 3 is a partial section view taken along line 3-3 in FIG. 1.

FIG. 4 is a plan view of a electrophysiology probe that may be used in combination with the positioning wrap illustrated in FIG. 1.

FIG. 5 is a section view showing the electrophysiology probe illustrated in FIG. 5 inserted through the positioning wrap illustrated in FIG. 1.

FIG. 6 is a section view taken along line 6-6 in FIG. 5.

FIG. 7 is a top view of a portion of the positioning wrap illustrated in FIG. 1 with the energy transmission element removed.

FIG. 8 is a perspective view showing a surgical system including the positioning wrap apparatus illustrated in FIG. 1.

FIG. 9 is perspective view showing a continuous lesion formed around the pulmonary veins.

FIG. 10 is a side view of an electrophysiology probe positioning wrap in accordance with a preferred embodiment of a present invention.

FIG. 11 is a section view taken along line 11-11 in FIG. 10.

FIG. 12 is a partial section view taken along line 12-12 in FIG. 10.

FIG. 12A is a section view of a hemostasis valve.

FIG. 13 is a side view of an electrophysiology probe positioning wrap in accordance with a preferred embodiment of a present invention.

FIG. 14 is a section view taken along line 14-14 in FIG. 13.

FIG. 15 is a partial section view taken along line 15-15 in FIG. 13.

FIG. 16 is a side view of an electrophysiology probe positioning wrap in accordance with a preferred embodiment of a present invention.

FIG. 17 is a section view taken along line 17-17 in FIG. 16.

FIG. 18 is a plan view of the positioning wrap illustrated in FIG. 16.

FIGS. 19A, 19C, 19E and 19G are top views of portions of electrophysiology probe positioning wraps in accordance with preferred embodiments of present inventions with the energy transmission elements removed.

FIGS. 19B, 19D, 19F and 19H are section views respectively taken along line 19B-19B in FIG. 19A, line 19D-19D in FIG. 19C, line 19F-19F in FIG. 19E and line 19H-19H in FIG. 19G.

FIG. 19I is a section view of an electrophysiology probe positioning wrap in accordance with a preferred embodiment of a present invention.

FIG. 20 is a side view of an electrophysiology probe positioning wrap in accordance with a preferred embodiment of a present invention.

FIG. 21 is a section view taken along line 21-21 in FIG. 20.

FIG. 22 is a side view of the positioning wrap illustrated in FIG. 20 in a loop orientation.

FIG. 23 is a side view of an electrophysiology probe positioning wrap in accordance with a preferred embodiment of a present invention.

FIG. 24 is a top view of a portion of the positioning wrap illustrated in FIG. 23.

FIG. 25 is a bottom view of a portion of the positioning wrap illustrated in FIG. 23.

FIG. 26 is a side view of the positioning wrap illustrated in FIG. 23 in a loop orientation.

FIG. 27 is a side view of an electrophysiology probe positioning wrap in accordance with a preferred embodiment of a present invention.

FIG. 28 is a section view taken along line 28-28 in FIG. 27.

FIG. 29 is a partial side view of an electrophysiology probe positioning wrap in accordance with a preferred embodiment of a present invention.

FIG. 30 is a side view of a portion of an electrophysiology probe positioning wrap and an insulation sleeve in accordance with a preferred embodiment of a present invention.

FIG. 31 is a side view of a portion of an electrophysiology probe positioning wrap and an insulation sleeve in accordance with a preferred embodiment of a present invention.

FIG. 32 is a section view taken along line 32-32 in FIG. 31.

FIG. 32A is a section view of a positioning wrap in accordance with a preferred embodiment of a present invention.

FIG. 32B is a top view of a portion of a positioning wrap in accordance with a preferred embodiment of a present invention.

FIG. 34 is a plan view of a clamp in accordance with a preferred embodiment of a present invention.

FIG. 35 is a section view taken along line 35-35 in FIG. 34.

FIG. 36 is a top view of a portion of the clamp illustrated in FIG. 34.

FIG. 38 is a side, partial section view of a portion of the tissue coagulation assembly illustrated in FIG. 37.

FIG. 39 is a section view taken along line 39-39 in FIG. 38.

FIG. 40 is a section view taken along line 40-40 in FIG. 38.

FIG. 41 is a section view taken along line 41-41 in FIG. 38.

FIG. 42 is a section view taken along line 42-42 in FIG. 37.

FIG. 43 is a section view taken along line 43-43 in FIG. 37.

FIG. 46 is a perspective view of a surgical system in accordance with a preferred embodiment of a present invention.

FIG. 47 is a section view taken along line 47-47 in FIG. 46.

FIG. 48 is an end view of the insulation element illustrated in FIG. 46.

FIG. 49 is a bottom view of a portion of the tissue surgical system illustrated in FIG. 46.

FIG. 50 is a plan view of a portion of the surgical probe illustrated in FIG. 46.

FIG. 51 is a section view taken along line 51-51 in FIG. 50.

FIG. 52 is a section view taken along line 52-52 in FIG. 50.

DETAILED DESCRIPTION OF THE PREFERRED EMBODIMENTS

Figure 33:
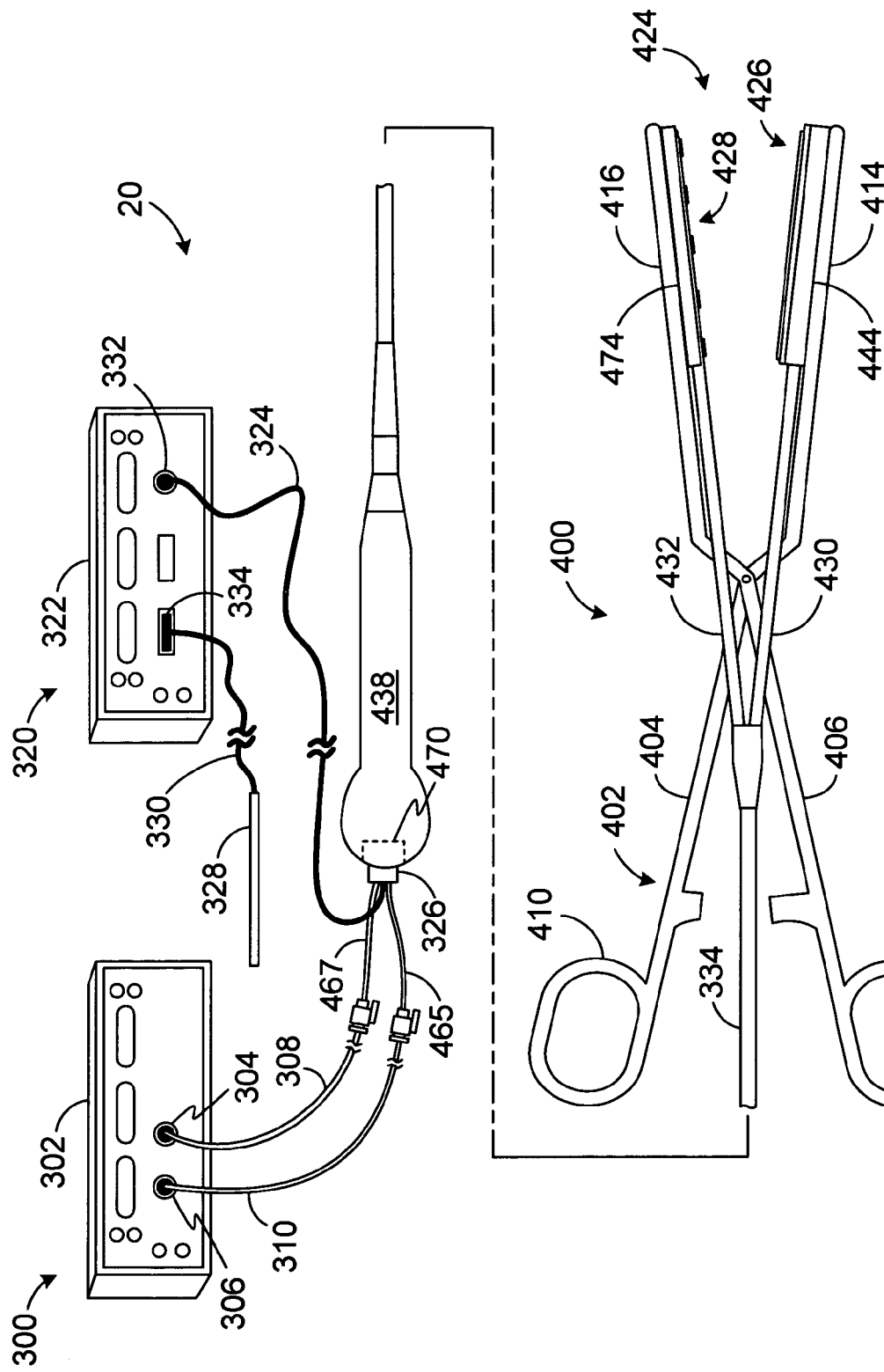
FIG. 33 is a perspective view of a surgical system in accordance with a preferred embodiment of a present invention.

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:

I. Introduction

II. Exemplary Electrophysiology Probe Positioning Wraps Capable of Being Secured Around an Organ III. Exemplary Clamp Based Lesion Formation Apparatus IV. Exemplary Probe Based Lesion Formation Apparatus The section titles and overall organization of the present detailed description are for the purpose of convenience only and are not intended to limit the present inventions.

I. Introduction

This specification discloses a number of structures, mainly in the context of cardiac treatment, because the structures are well suited for use with myocardial tissue. Nevertheless, it should be appreciated that the structures are applicable for use in therapies involving other types of soft tissue. For example, various aspects of the present inventions have applications in procedures concerning other regions of the body such as the prostate, liver, brain, gall bladder, uterus, breasts, lungs, esophagus, and other solid organs.

Additionally, although the exemplary implementations are described below in the context of lesion formation regions that transmit radio-frequency energy to tissue, either directly or by way of a conductive fluid, the present inventions are not so limited. Other lesion formation regions, such as those formed by laser arrays, ultrasonic transducers, microwave electrodes, and ohmically heated hot wires, may be employed with suitably configured insulation elements. Lesion formation regions may also be formed with one or more cryotemperature devices, or needle projections for chemical ablation (which are preferably about 1 to 2 mm in length), and combined with suitably configured insulation elements.

II. Exemplary Electrophysiology Probe Positioning Wraps Capable of Being Secured Around an Organ An electrophysiology probe positioning wrap (or "positioning wrap") 100 in accordance with one embodiment of a present invention is illustrated in FIGS. 1-3 and 5-7. The illustrated embodiment includes an insulation element 102, an energy transmission element 104 and a connector device 106 that may be used to position the longitudinal ends of the energy transmission element adjacent to one another. The insulation element 102, which is provided with a probe lumen 108, may be used to hold an electrophysiology probe 230 (FIG. 4) and to prevent coagulation of non-target tissue. The insulation element 102 also prevents rolling and slipping and facilitates the formation of a linear lesion. The exemplary electrophysiology probe 230 includes a probe body 232, a plurality of electrodes 234 (or other energy emission elements) carried on the distal portion of the probe body, a handle 236 at the proximal end of the probe body, and a pull wire 238 at the distal end of the probe body.

Tissue coagulation energy from the electrodes 234 is transferred to, and through, the energy transmission element 104 by electrically conductive fluid. To that end, the inner diameter of the probe lumen 108 is slightly greater than the outer diameter of the probe body 232. When the electrophysiology probe 230 is inserted into one end of the positioning wrap 100 to such an extent that the distal end of the probe body 232 reaches the other end (FIG. 5), a fluid transmission space 110 will be defined between the probe body and the inner surface of the probe lumen 108. The insulation element 102 also includes a fluid slot 112 that extends from the fluid transmission space 110 to the energy transmission element 104. Preferably, the electrodes 234 will be carried on the electrophysiology probe 230 such that the electrodes will, as a group, extend from one end of the fluid slot 112.

It should be noted that despite the fact that the energy transmission element 104 extends from one side of the insulation element 102 to the other, ablation is limited to the area adjacent to the fluid slot 112. This is because current tends to follow the path of least resistance to ground potential, which in this case is from the electrodes 234, though the slot 112, to the tissue.

The positioning wrap 100 also includes seals that prevent leakage from the fluid transmission space 110. In the embodiment illustrated in FIGS. 1-3 and 5-7, fluidic seals 114 and 116 are formed in the insulation element 102. The inner diameter of the fluidic seals 114 and 116 is slightly less than the outer diameter of the probe body 232. As such, the fluidic seals 114 and 116 will engage with probe body 232 and seal the longitudinal ends of the fluid transmission space 110. The fluidic seals 114 and 116 are created by reducing the diameter of the probe lumen 108 at the longitudinal ends of the insulation element 102. A pair of rings 118 helps to maintain the seals around the probe body 232.

In addition to the probe lumen 108, the exemplary positioning wrap 100 is provided with fluid lumens 120 and 122 (FIGS. 2, 3 and 5). The fluid lumens 120 and 122, which are connected to one end of the probe lumen 108, may be used for fluid ventilation when fluid is infused into the positioning wrap 100 by way of the probe lumen, or may be used for infusion when fluid is ventilated from the positioning wrap by way of the probe lumen. The probe lumen 108 and the fluid lumens 120 and 122 are connected to respective tubes that are used to infuse and ventilate fluid to and from the lumens. Referring to FIGS. 1, 3 and 5, in the illustrated embodiment, the probe lumen 108 is connected to a tube 124 that passes through an aperture 126 in the insulation element 102. The fluid lumens 120 and 122 are connected to tubes 128 and 130 that extend directly into the fluid lumens by way of openings 132 and 134. The tubes 128 and 130 are connected to a common tube 136 by a connector 138. Stopcocks 140 and 142 are provided on the ends of the tubes 124 and 136.

The surfaces of probe lumens in accordance with present invention may be configured such that they are smooth and continuous from one end to another. As illustrated in FIGS. 6 and 7, however, the inner surface of the probe lumen 108 in the exemplary positioning wrap 100 includes a plurality of protrusions 144 and channels 146. The protrusions 144 and channels 146 perform a variety of functions. For example, the protrusions 144 and channels 146 reduce the amount of surface area that may come into contact with the probe body 232, thereby reducing the amount of friction that will be present as the probe body is fed into, and pulled out of, the positioning wrap 100. The protrusions 144 and channels 146 also insure that fluid flow will not be restricted in those instances where the probe lumen 108 collapses slightly. Other exemplary lumen surface configurations are discussed below with reference to FIGS. 19A-19H.

Referring to FIGS. 1, 2 and 8, the exemplary connector device 106 is a relatively thin, flexible elongate device that includes a main portion 148 and a pair of end portions 150 and 152. The main portion 148 is secured to the insulation element 102, preferably along the entire length of the insulation element. The end portions 150 and 152, which extend from the longitudinal ends of insulation element 102, may be used to pull the lesion formation apparatus 100 into the orientation illustrated in FIG. 8 and then tied onto a knot 154 to hold the lesion formation apparatus in place. The end portions 150 and 152 may also be provided with knots, beads, eyelets and/or any other closure mechanism that can be used to hold the end portions (as well as the longitudinal ends of the insulation element 102) in the orientation illustrated in FIG. 8.

The positioning wrap 100 and electrophysiology probe 230 may be employed in the exemplary surgical system 10 illustrated in FIG. 8, which may also include a fluid supply and control apparatus 300 and a power supply and control apparatus 320. The fluid supply and control apparatus 300, which may be used to supply electrically conductive fluid to any of the devices described herein that use such fluid, includes housing 302, a fluid outlet port 304, and a fluid inlet port 306. The fluid outlet port 304 may be coupled to the stopcock 140 (and, therefore, to the probe lumen 108) by a connector tube 308, while the fluid inlet port 306 may be coupled to the stopcock 142 (and, therefore, to the fluid lumens 120 and 122) by a connector tube 310. An infusion pump capable of variable flow rates is one example of a suitable fluid supply and control apparatus.

The power supply and control apparatus 320 includes an electrosurgical unit ("ESU") 322 that supplies and controls RF power. A suitable ESU is the Model 4810A ESU sold by Boston Scientific Corporation of Natick, Mass., which is capable of supplying and controlling power on an electrode-by-electrode basis. With respect to temperature sensing, temperature at the electrodes 234 may be determined by measuring impedance at each electrode or by including temperature sensors on the probe 230. The ESU 322 transmits energy to the electrodes 234 by way of a cable 324 and a connector 326, which may be connected to a PC board in the probe handle 236. The amount of power required to coagulate tissue ranges from 5 to 150 W. Tissue coagulation energy emitted by the electrodes 234 is returned through one or more indifferent electrodes 328 that are externally attached to the skin of the patient with a patch, or one or more electrodes (not shown) that are positioned in the blood pool, and a cable 330. The cables 324 and 330 are configured to be connected to differently sized connectors 332 and 334 on the ESU 322 in order to prevent improper connections.

The positioning wrap 100 may be positioned around portions of organs during lesion formation procedures performed with the surgical system 10. For example, one method of treating focal atrial fibrillation with the positioning wrap 100 involves the creation of transmural lesions around the pulmonary veins. Lesions may be created around the pulmonary veins individually, in pairs, or, as is illustrated in FIG. 9, a single transmural epicardial lesion L may be created around all four of the pulmonary veins PV. Such a lesion may be formed by positioning the positioning wrap 100 around the pulmonary veins PV in the manner illustrated in FIG. 8. The connector device 106 may be used to secure the longitudinal ends of the energy transmission element 104 in close proximity to one another. Although there is a slight space between the ends of the energy transmission element 104 in FIG. 8 in order to more clearly show various elements of the illustrated embodiment, the ends would typically be in contact with one another or slightly overlap in actual use. Typically, the pull wire 238 at the distal end of the probe body 232 will have been pulled through the positioning wrap 100 prior to it being positioned around the pulmonary veins PV or other target tissue area.

Once the positioning wrap 100 is in place, the probe body 232 may be pulled through the probe lumen 108 with the pull wire 238 until both of the fluidic seals 114 and 116 have engaged portions of the probe body. Alternatively, the probe body 232 may be pulled through the probe lumen 108 prior to positioning the wrap 100 around the pulmonary veins PV or other target tissue area. The fluid transmission space 110 and fluid slot 112 are then filled with conductive fluid from the fluid supply and control apparatus 300. The fluid may be continuously infused and ventilated by way of the tubes 124, 128, 130, 308 and 310 or, alternatively, fluid flow may be stopped after the fluid transmission space 110 and slot 112 have been filled. Tissue coagulation energy is then transmitted from the power supply and control apparatus 320 to one, some or all of the electrodes 234. The energy will flow through the conductive fluid and energy transmission element 104 to create a lesion in the vicinity of the fluid slot 112. Preferably, the electrodes 234 will as a group be coextensive with the entire target tissue area. In those instances where the electrodes 234 are not coextensive with the entire target tissue area, the probe body 232 may be indexed after a portion of the lesion is formed by pulling on the pull wire 238 (or handle 236) in order to move the electrodes 234 to another portion of the target tissue area. Tissue coagulation energy will then be transmitted from the power supply and control apparatus 320 to one, some or all of the electrodes 234 to form another portion of the lesion. This process will continue until the lesion is complete.

Although the present inventions are not limited to any particular materials, suitable materials for the insulation element 102 include flexible polymer (elastomer) open and closed cell foams. In those instances where open cell foams are used, the base member may include a sealing skin (not shown) to prevent fluid absorption. Flexible thermoplastics and thermoset polymers may also be employed. Materials that have a hardness rating of ≅to 35 (Shore A) are preferred. In addition to protecting adjacent tissue from the tissue coagulation energy, the insulation element makes the positioning wrap 100 "one directional" in that energy will only be transferred through the slot 112. Such an arrangement is more efficient than one in which the energy transfer can take place along the entire perimeter of the electrodes 234.

Turning to the energy transmission element 104, a hydrophilic conductive polymer film that is about 0.002 to 0.008 inch thick is one example of a suitable energy transmission element. Although the polymer film is electrically non-conductive, the relatively small pores of this material allow effective ionic transport in response to the applied RF field. At the same time, the relatively small pores prevent transfer of macromolecules through the material, so that pressure driven liquid perfusion is less likely to accompany the ionic transport, unless relatively high pressure conditions develop within positioning wrap. Hydro-Fluoro™ material, which is disclosed in U.S. Pat. No. 6,395,325, is one material that may be used. Materials such as nylons (with a softening temperature above 100° C.), PTFE, PEI and PEEK that have micropores created through the use of lasers, electrostatic discharge, ion beam bombardment or other processes may also be used. Such materials would preferably include a hydrophilic coating. Nanoporous to microporous materials may also be fabricated by weaving a material (such as nylon, polyester, polyethylene, polypropylene, hydrophilic copolymers, expanded PTFE, fluorocarbon, glass, cotton, or other fiber) into a mesh having the desired pore size and porosity. Regenerated cellulose membrane materials, typically used for blood oxygenation, dialysis or ultrafiltration, are other examples of suitable nanoporous material for the energy transmission element 104.

Pore diameters smaller than about 1-10 nanometers retain macromolecules, but allow ionic transfer through the pores in response to the applied RF field. With smaller pore diameters, pressure driven liquid perfusion through the pores is less likely to accompany the ionic transport, unless relatively high pressure conditions develop within the energy transmission element 104. Larger pore diameters (up to 8 µm) can also be used to permit ionic current flow across the membrane in response to the applied RF field. With larger pore diameters, pressure driven fluid transport across the energy transmission element 104 is much higher. Where a larger pore diameter is employed, thereby resulting in significant fluid transfer (or "weeping") through the energy transmission element 104, a saline solution having a sodium chloride concentration of about 0.9% weight by volume would be preferred. Such weeping reduces impedance and tissue desiccation.

With respect to porosity, which represents the volumetric percentage of the energy transmission element 104 that is composed of pores and not occupied by the casing material, the magnitude of the porosity affects electrical resistance. Low-porosity materials have high electrical resistivity, whereas high-porosity materials have low electrical resistivity. The porosity of the energy transmission element 104 should be at least 1% for epicardial applications employing a 1 to 5 µm pore diameter.

The electrical resistivity of the energy transmission element 104 will have a significant influence on lesion geometry and controllability. Low-resistivity (below about 500 ohm-cm) requires more RF power and results in deeper lesions, while high-resistivity (at or above about 500 ohm-cm) generates more uniform heating and improves controllability. Because of the additional heat generated by the increased resistivity within the energy transmission element 104, less RF power is required to reach similar surface tissue temperatures after the same interval of time. Consequently, lesions generated with high-resistivity structures usually have smaller depth. The electrical resistivity of the energy transmission element 104 can be controlled by specifying the pore size of the material, the porosity of the material, and the water adsorption characteristics (hydrophilic versus hydrophobic) of the material. A detailed discussion of these characteristics is found in U.S. Pat. No. 5,961,513. A suitable electrical resistivity for epicardial lesion formation is about 1 to 3000 ohm-cm measured wet.

Turning to water absorption characteristics, hydrophilic materials are generally preferable because they possess a greater capacity to provide ionic transfer of RF energy without significant liquid flow through the material.

The electrically conductive ionic fluid preferably possesses a low resistivity to decrease ohmic loses, and thus ohmic heating effects, within the positioning wrap. The composition of the electrically conductive fluid can vary. In the illustrated embodiment, the fluid is a hypertonic saline solution, having a sodium chloride concentration at or near saturation, which is about 5% to about 25% weight by volume. Hypertonic saline solution has a relatively low resistivity of only about 5 ohm-cm, as compared to blood resistivity of about 150 ohm-cm and myocardial tissue resistivity of about 500 ohm-cm. Alternatively, the ionic fluid can be a hypertonic potassium chloride solution. With respect to temperature and flow rate, a suitable inlet temperature for epicardial applications (the temperature will, of course, rise as heat is transferred to the fluid) is about 0 to 25° C. with a constant flow rate of about 2 to 10 ml/min.

One suitable material for the connector device 106 is thin (e.g. about 0.005 inch to 0.025 inch) woven fabric ribbon. This material is relatively soft and will not slice through tissue during use. Other suitable materials include polymer films and cords. The main portion 148 may be secured to the insulation element 102 with a flexible adhesive (not shown) such as polyurethane or a Polycin® and Vorite® mixture.

The overall dimensions of positioning wraps in accordance with the present inventions will, of course, depend on the intended application. In one exemplary implementation that is suitable for forming epicardial lesions around the pulmonary veins, the insulation element 102 is about 15 cm to 30 cm in length. The aspect ratio, i.e. the width to thickness (or height) ratio, is about 2-3 to 1. Typically, in the orientation illustrated in FIG. 2, the width of the insulation element 102 is about 7 mm to 20 mm and the thickness is about 3 mm to 10 mm. With respect to the exemplary connector device 106, the width will correspond to that of the associated side of the insulation element 102 and, accordingly, is about 5 mm to 16 mm. The end portions 150 and 152 extend about 15 cm to 60 cm from the longitudinal ends of the insulation element 102. The fluid slot 112 will typically be about 1 to 3 mm wide. As a result, there will be relatively wide (e.g. about 2 mm to 9.5 mm) insulation element portions on either side of the fluid slot 112 that will insulate the tissue associated therewith from levels of coagulation energy that are great enough to coagulate tissue during the creation of a typical lesion (i.e. about 50 to 180 seconds). In the context of a pulmonary vein isolation procedure such as that described above with reference to FIGS. 8 and 9, it is desirable to have about 5-10 mm between the lesion and the pulmonary veins in order to minimize stenosis risk.

Another exemplary positioning wrap is generally represented by reference numeral 100a in FIGS. 10-12A. The positioning wrap 100a is substantially similar to the positioning wrap 100 described above with reference to FIGS. 1-3 and 5-8 and similar elements are represented by similar reference numerals. With respect to the differences, the insulation element 102a has an overall tapered shape in cross-section and a smooth probe lumen 108a. The tapered shape of the insulation element 102a keeps the wrap 100a from buckling, keeps the slot 112 open, and gives maximum contact along the length of slot. The thin edges provide flexibility. The insulation element 102a is also configured such that it has a closed end 156. As such, a probe (such as the exemplary probe 230 without the pull wire 238 and the electrodes 204 closer to the distal end) will simply be fed into the positioning wrap 100a until it reaches the closed end 156. This arrangement eliminates the need for a fluidic seal (e.g. the seal 116) at that end of the insulation element 102a. The exemplary insulation element 102a also lacks a fluidic seal at the other end. Instead, the positioning wrap 100a is provided with a hemostasis valve 158 that includes a seal 160 (FIG. 12A). The hemostasis valve 158 is connected to a tube 162, which extends into the probe lumen 108a by way of an aperture 164, and to a tube 166, which extends to the stopcock 140.

The positioning wrap 100a operated in substantially the same way as the positioning wrap 100. For example, the positioning wrap 100a may be positioned in the manner illustrated in FIG. 8 with or without the electrode supporting probe already in place within the probe lumen 108a. In those instances where the probe is not within the positioning wrap 100a prior to positioning, the probe may be fed into the wrap after it is positioned. Thereafter, conductive fluid may be infused (or ventilated) through the hemostasis valve 158/tube 162, and ventilated (or infused) through the tubes 128 and 130. Tissue coagulation energy is then transmitted from the power supply and control apparatus to one, some or all of the electrodes on the probe to form a lesion.

Still another exemplary positioning wrap is generally represented by reference numeral 100b in FIGS. 13-15. The positioning wrap 100b is substantially similar to the positioning wraps 100 and 100a described above with reference to FIGS. 1-3, 5-8 and 10-12A and similar elements are represented by similar reference numerals. With respect to the differences, the insulation element 102b has an overall shape that is similar to the insulation element 100, but lacks the fluid lumens 120 and 122. The fluid lumens 120 and 122 are unnecessary in the positioning wrap 100b because the conductive fluid is not being infused and ventilated from the same end of the wrap. The conductive fluid instead flows in one end of the probe lumen 108b and out the other. To that end, the positioning wrap 100b is provided with a pair of hemostasis valves 158 and 168. As noted above, the hemostasis valve 158 is connected to tubes 162 and 166. Tube 162 extends into the probe lumen 108b, while tube 166 extends to the stopcock 140. The hemostasis valve 168, which is identical to valve 158 includes a seal (not shown), and is connected to a tube 170 that extends into the probe lumen 108b by way of an aperture 172. The hemostasis valve 168 is also connected to the stopcock 142 by a tube 174.

The positioning wrap 100b operated in substantially the same way as the positioning wrap 100. For example, the positioning wrap 100b may be positioned in the manner illustrated in FIG. 8 with or without the electrode supporting probe already in place within the probe lumen 108b. In those instances where the probe is not within the positioning wrap 100b prior to positioning, the probe 230 may be pulled through the wrap with the pull wire 238 (note FIG. 15) after the wrap is positioned. Thereafter, conductive fluid may be infused (or ventilated) through the hemostasis valve 158/tube 162, and ventilated (or infused) through the hemostasis valve 168/tube 172. Tissue coagulation energy is then transmitted from the power supply and control apparatus to one, some or all of the electrodes 234 on the probe 230 to form a lesion.

The exemplary positioning wrap 100c illustrated in FIGS. 16-18 is substantially similar to the positioning wraps 100 and 100a described above with reference to FIGS. 1-3, 5-8 and 10-12A and similar elements are represented by similar reference numerals. The overall cross-sectional shape of the insulation element 102c is, for example, similar to that of the insulation element 102. The positioning wrap 100c also employs a hemostasis valve 158 and has a closed end, as does the positioning wrap 100a. With respect to the primary differences, the positioning wrap 100c includes suction capability and tissue stimulation and/or sensing capabilities. The suction capability may be used to fix the position of the positioning wrap 100c relative to the target tissue. Tissue stimulation and sensing may be used to confirm whether or not a therapeutic lesion has been formed by, for example, supplying tissue stimulation energy on one side of a lesion and/or monitoring tissue (either electrically or visually) on the other side of the lesion. Tissue stimulation may also be used to determine lesion depth and, correspondingly, whether or not a lesion is transmural. The energy transmission element 104c is also slightly different than the energy transmission element 104 in that the energy transmission element 104c is relatively narrow (i.e. slightly wider than the fluid slot 112) so that it does not interfere with the suction and tissue stimulation and/or sensing.

With respect to suction, the positioning wrap 100c includes a plurality of suction ports 176 on opposite sides of the energy transmission element 104c. A pair of internal suction lines 178 are formed in the insulation element 102c and each of the suction ports 176 is connected to a suction line by a suction aperture 180. The suction lines 178 are also connected to a connector 182 such as, for example, the illustrated Luer connector. A suction source 340 (FIG. 16) may be connected to the connector 182 by a flexible tube 342. When the suction source 340 is actuated, the suction ports 176 will fix the position of the positioning wrap 100c relative to the target tissue.

A plurality of fluid apertures (not shown), which are connected to the probe lumen 108 or to the fluid lumens 120/122, may be provided between the slot 112 and the suction ports 176. These fluid apertures may be used to weep fluid that hydrates the tissue and prevents desiccation, and also improves RF coupling, suction seal and temperature sensing.

Turning to tissue stimulation and sensing, the positioning wrap 100c includes tissue stimulation electrodes 184 and, in some instances, sensing electrodes 186. In the exemplary implementation, the stimulation and sensing electrodes 184 and 186 are located adjacent to the suction ports 176 on opposite sides of the fluid slot 112 and the energy transmission element 104c. As such, the tissue stimulation and sensing electrodes 184 and 186 will be on opposite sides of the lesion formed by the energy passing through the energy transmission element 104c. The electrodes 184 and 186, which are held firmly against tissue when the suction source 340 is activated, are relatively small, e.g. 0.5 mm to 1 mm in diameter and about 0.01 mm thick. Although not required, the stimulation and sensing electrodes 184 and 186 are also arranged in bipolar pairs in the exemplary implementation. Other electrode arrangements include, but are not limited to, arrangements with greater or fewer numbers of bipolar pairs and unipolar arrangements where a single electrode is positioned adjacent to each of the suction ports 176.

The tissue stimulation and sensing electrodes 184 and 186 may be formed by coating a conductive material onto the insulation element 102c using conventional coating techniques or an IBAD process. Suitable conductive materials include platinum-iridium and gold. An undercoating of nickel, silver or titanium may be applied to improve adherence. Conductive ink compounds, such as silver-based flexible adhesive conductive ink (polyurethane binder) or metal-based adhesive conductive inks (e.g. platinum, gold, or copper based) may also be pad printed onto the insulation element 102c.

Respective sets of signal lines (not shown) extend from the stimulation and sensing electrodes 184 and 186, through the signal line lumens 188 and 190 to a cable 192. The cable 192 is connected to an EP recording apparatus 350 and the EP recording apparatus is connected to, and directs the tissue stimulation and recording associated with, a tissue stimulation apparatus 360 (FIG. 16). A suitable EP recording apparatus 350 is the Prucka CardioLab 7000® from GE Medical Systems. One exemplary type of tissue stimulation apparatus 360 is a conventional pacing apparatus, such as the Medtronic Model Nos. 5330 and 5388 external pulse generators. The power delivered to tissue for stimulation purposes will typically be significantly less than that which would form a transmural or otherwise therapeutic lesion in tissue. An exemplary stimulation energy delivery would consist of two stimulation pulses per second, each pulse being 1 millisecond. The maximum amplitude would be 10 mA, which would create 5 V, for a total power delivery of 100 µW, as compared to the 5 to 150 W required to coagulate tissue.

With respect to lesion formation, the positioning wrap 100c operated in a similar manner to the positioning wrap 100a. For example, the positioning wrap 100c may be positioned in the manner illustrated in FIG. 8 with or without the electrode supporting probe already in place within the probe lumen 108a. The suction source 340 may then be actuated in order to insure that the positioning wrap 100c does not move and that there is good contact between the energy transmission element 104c and electrodes 184/186 and the tissue. In those instances where the probe is not within the positioning wrap 100c prior to positioning, the probe may be fed into the wrap after it is positioned. Conductive fluid may be infused (or ventilated) through the hemostasis valve 158/tube 162, and ventilated (or infused) through the tubes 128 and 130. Tissue coagulation energy is then transmitted from the power supply and control apparatus to one, some or all of the electrodes on the probe to form a lesion.

The stimulation and sensing electrodes 184 and 186 may then be used to determine whether or not a therapeutic lesion has been properly formed. For example, after the positioning wrap 100c has been used in the manner discussed above with reference to FIGS. 8 and 9 to form a pulmonary vein isolating lesion, one of the pairs of stimulation electrodes 184 may be used to supply a bipolar pacing pulse on the side of the lesion opposite the left atrium. The physician can determine whether or not a therapeutic lesion (or "complete block") has been formed by observing the left atrium. If the pacing pulse is able to cross the lesion, the heart will beat faster (e.g. 120 beats/minute). This may be determined by observation or by use of an ECG machine that is monitoring the heart. Here, additional coagulation will be required to complete the lesion. The failure to stimulate the heart from the side of the lesion opposite the left atrium is, on the other hand, indicative of the formation of a therapeutic lesion. Nevertheless, because muscle bundles are not always connected near the pulmonary veins, it is preferable that the stimulation energy be applied to a number of tissue areas, from a number of stimulation electrode pairs, on the side of the lesion opposite the left atrium to reduce the possibility of false negatives. The sensing electrodes 186, which are located on the opposite side of the lesion, may also be used to capture the stimulus from the pacing electrodes 184.

Alternatively, the sensing electrodes 186 may be used to monitor tissue within the region that was intended to be isolated. In the context of pulmonary vein isolation, for example, the sensing electrodes 186 may be placed in contact with viable tissue on the pulmonary vein side of the lesion. Local activation within the isolated region from the heart's natural stimulation is indicative of a gap in the lesion.

Additional details concerning tissue stimulation and sensing are provided in U.S. application Ser. No. 10/727,143, which is entitled "Surgical Methods And Apparatus For Forming Lesions In Tissue And Confirming Whether A Therapeutic Lesion Has Been Formed," and is incorporated herein by reference.

As noted above with reference to FIGS. 6 and 7, the inner surface of the probe lumen 108 in the exemplary positioning wrap 100 includes a plurality of square protrusions 144 and crisscrossing channels 146. The present inventions are not limited to such configurations and a variety of other configurations may be employed. By way of example, and not limitation, and referring first to FIGS. 19A and 19B, the exemplary insulation element 102d includes a plurality of ring shaped protrusions 144d extending inwardly from the surface of the probe lumen 108d. The probe lumen 108e in the exemplary insulation element 102e illustrated in FIGS. 19C and 19D includes a plurality of longitudinally extending protrusions 144e and channels 146e. Turning to FIGS. 19E and 19F, the insulation element 102f includes a probe lumen 108f with a plurality of semi-spherical protrusions 144f and a channel 146f that extends between the protrusions. The probe lumen 108g in the insulation element 102g includes a helical protrusion 144g and a helical channel 146g. The protrusions 144d-g should be sized such that there is a small gap between the protrusions and the probe (which is shown in dashed lines in FIGS. 19B, 19D, 19F and 19H).

Another exemplary insulation element is generally represented by reference numeral 102h in FIG. 19I. The insulation element 102h includes a plurality of reinforcing members 194, such as straight or pre-shaped polymer, composite or metal members, that prevent twisting of the positioning wrap, hold a shaped positioning wrap straight for introduction, or provide lumens (not shown) for temperature sensor wires or other elements. Although the probe lumen 108h is smooth, it may be configured in any of the other manners described above.

Insulation elements may also perform functions in addition to insulation and fluid transmission. As illustrated for example in FIGS. 20-22, the insulation element 102i in a positioning wrap 100i includes a pair of pre-shaped reinforcing members 196 (e.g. thin strips of Nitinol) with a pre-shaped loop configuration and a removable stylet 198 (e.g. a steel rod) that is straight and rigid enough to overcome the bending forces applied by pre-shaped reinforcing members 196. The removable stylet 198 is carried within a tube 200 that defines a longitudinally extending lumen within the insulation element 102i. Absent the presence of the straightening force applied by the removable stylet 198, the insulation element 102i, with its pre-shaped reinforcing members 196, will bend the positioning wrap 100i into the loop illustrated in FIG. 22 and will maintain the loop during lesion formation procedures. Additionally, although the probe lumen 108i is smooth, it may be configured in any of the other manners described above.

In the illustrated embodiment, the longitudinal ends of the energy transmission element 104 overlap slightly in order to insure that the lesion formed thereby will be a complete circle. Alternatively, pre-shaped reinforcing members 198 may be configured such that the longitudinal ends abut one another, or such that there is a gap between the longitudinal ends, if the intended application so requires. Additionally, although the illustrated reinforcing member has a substantially circular shape, any shape suitable for the intended application (e.g. a U-shape) may be employed. A pre-shaped reinforcing member(s) and stylet arrangement may be incorporated into any of the positioning wraps described herein with reference to FIGS. 1-19h. Moreover, pre-shaping may also be accomplished without the use of reinforcing members by, for example, molding the insulation element into the desired shape.

During use, the removable stylet 198 will be in place within the tube 200 prior to deployment of the positioning wrap 100i. The removable stylet 198 will be withdrawn in the direction of arrow A (FIG. 20) as the wrap is advanced in a direction tangential to the target tissue structure, thereby allowing the pre-shaped reinforcing members 196 to bend the wrap into a loop shape around the target structure. The stylet 198 is preferably slightly longer than the insulation element 102i in order to provide a free end that may be grasped by the physician. The stylet 198 may, in some instances, have a slight curvature where applications so require.

In addition to bending the positioning wrap 100i into the bent orientation illustrated in FIG. 22, the pre-shaped reinforcing members 196 will maintain the positioning wrap in the bent orientation during lesion formation procedures. As such, the connector device 106 need not be used (although it may be used if desired) to maintain the positioning wrap in the loop orientation. The end portions 150 and 152 may still be used, however, to pull the positioning wrap around a tissue structure as it is being positioned for a procedure.

As illustrated above, the configuration of the insulation element is susceptible to a wide degree of variation. There are also a number of alternative connector configurations. Turning to FIGS. 23-26, the exemplary positioning wrap 100j is substantially similar to the positioning wrap 100 described above with reference to FIGS. 1-9 and similar elements are represented by similar reference numerals. Here, however, the positioning wrap 100j includes a fastener 202 that may be used instead of, or in addition to, the connector device 106 when fixing the position of the wrap around an organ.

The fastener 202 includes a pair of fastening elements 204 and 206 that are associated with the longitudinal ends of the insulation element 102. The exemplary fastening elements 204 and 206 are hook and loop fastener strips, such as Velcro® strips. Fastening element 204 is carried on the bottom of the connector device main portion 148 and faces downwardly (in the orientation illustrated in FIG. 23), while the fastening element 206 is carried by a support 208 that is secured to the connector device main portion and faces upwardly. So arranged, the fastening elements 204 and 206 will face one another, thereby allowing them to be connected to one another, when the positioning wrap 100j is bent into a loop in the manner illustrated in FIG. 26.

The exemplary fastener 202 may also be used in combination with the positioning wraps described above with reference to FIGS. 10-22.

Other exemplary fastening elements include devices that will hold the connector device end portions 150 and 152, such as clamps and spring-biased locks. In those instances where the end portions 150 and 152 include knots, cleats (i.e. a tube with slots that receive the knots) may be employed.

Another exemplary positioning wrap is generally represented by reference numeral 100k in FIGS. 27 and 28. The positioning wrap 100k is substantially similar to the positioning wrap 100 described above with reference to FIGS. 1-9 and similar elements are represented by similar reference numerals. Here, however, the connector device 106k includes a pair of flexible pull strings 210 and 212 and a pair of flexible end strings 214 and 216. The pull strings 210 and 212 are secured to the insulation element 102, and preferably along the entire length of the insulation element, with adhesive 218. The longitudinal ends of the pull strings 210 and 212 are secured to one another, and to the end strings 214 and 216, by knots 220 (or other fastening methods). The connector device 106k may also be used in place of the connector device 106 in the positioning wraps described above with reference to FIGS. 10-26.

The exemplary positioning wraps illustrated in FIGS. 1-3 and 5-28 may also be configured in a manner that will help the physician distinguish various elements from one another. For example, the positioning wrap 100l illustrated in FIG. 29, which is essentially identical to the wrap 100 described above with reference to FIGS. 1-9, includes a connector device 106l that is relatively dark in color, while the insulation element 102 is relatively light in color. This may also be reversed, with the insulation element 102 formed from a relatively dark material and the connector device 106l formed from a relatively light material. The color of the insulation element 102 may also be selected so as to help the physician identify various apparatus elements during surgical procedures. Stripes and other patterns may also be employed. A visible scale may also be provided on the insulation element or the connector device in order to allow the physician to monitor and manage the full length of the apparatus during the procedure.

The exemplary lesion formation apparatus described above with reference to FIGS. 1-29 may also be provided with a movable insulation device that prevents some of the tissue that would otherwise be ablated by the coagulation energy from being ablated. As illustrated for example in FIG. 30, a slidable insulation sleeve 222 is positioned around a portion of the positioning wrap 100. The length of the insulation sleeve 222 will vary from application to application, but will typically be longer that the insulation element 102 itself and up to twice the length of the insulation element. This allows the insulation sleeve 222 to provide an electrically insulative barrier between the energy transmission element 104 and the patient, from the exterior of the body to the target tissue region. Suitable materials for the insulation sleeve include silicone, polyurethane, thin film Kapton®, PTFE impregnated fabric and polyester. The insulation sleeve 222 may, for example, be used to cover the majority of the energy transmission element 104 during touch up procedures to fill in gaps in lesions. Here, the insulation sleeve 222 may be pulled proximally until the desired length of the energy transmission element 104 is exposed.

In an alternative configuration, which is illustrated in FIGS. 31 and 32, the exemplary insulation sleeve 224 includes a window 226 that allows small lesions to be formed in specific locations. Sleeve 224 is also configured to prevent the positioning wrap 100 from rotating and to insure that the energy transmission element 104 is aligned with the window 226. More specifically, the surface 228 of the insulation sleeve internal lumen is shaped in a manner substantially similar to the insulation element 102.

Temperature sensors may also be provided on the positioning wraps described above with reference to FIGS. 1-29. For example, the positioning wrap 100m illustrated in FIGS. 32A and 32B, which is essentially identical to the wrap 100, includes a plurality of temperature sensors 227 between the insulation element 102m and the narrower energy transmission element 104c. The temperature sensors 227 are located on each side of the fluid slot 112, preferably relatively close (e.g. within 0.5 to 1.5 mm) to the slot. Suitable temperature sensors include, but are not limited to, thermocouples and thermistors. The insulation element 102m also includes a pair of lumens 229 for the signal wires (not shown) that extend over the top of energy transmission element 104c and are respectively connected to the temperature sensors 227. The signal wires are associated with a cable and connector (not shown) arrangement that extends from one end of the positioning wrap 100m and may be connected to the power supply and control device that is supplying energy to the probe being used in combination with the wrap.

In the exemplary positioning wraps described above with reference to FIGS. 1-29, the fluid slots 112 are located along the centerline of the insulation element and, accordingly, the width of the insulated regions on either side of the fluid slots are equal. It should be noted, however, that this is not required and the above-described positioning wraps may be reconfigured if applications so require such that there is a wider insulated area on one side of the fluid slot 112 than the other.

III. Exemplary Clamp Based Lesion Formation Apparatus

As illustrated for example in FIG. 33, an exemplary surgical system 20 in accordance with one embodiment of a present invention includes the fluid supply and control apparatus 300, the power supply and control apparatus 320, and an electrophysiology clamp apparatus 400. The clamp apparatus 400 includes a clamp and a tissue coagulation assembly that may be secured to the clamp. As used herein, the term "clamp" includes, but is not limited to, clamps, clips, forceps, hemostats, and any other surgical device that includes a pair of opposable clamp members that hold tissue, at least one of which is movable relative to the other. In some instances, the clamp members are connected to a scissors-like arrangement including a pair of handle supporting arms that are pivotably connected to one another. The clamp members are secured to one end of the arms and the handles are secured to the other end. Certain clamps that are particularly useful in minimally invasive procedures also include a pair of handles and a pair of clamp members. Here, however, the clamp members and handles are not mounted on the opposite ends of the same arm. Instead, the handles are carried by one end of an elongate housing and the clamp members are carried by the other. A suitable mechanical linkage located within the housing causes the clamp members to move relative to one another in response to movement of the handles. The clamp members may be linear or have a predefined curvature that is optimized for a particular surgical procedure or portion thereof. The clamp members may also be rigid or malleable.

One example of a clamp that may be employed in the electrophysiology clamp apparatus 400 is generally represented by reference numeral 402 in FIGS. 33-36. Referring more specifically to FIGS. 34-36, the clamp 402 includes a pair of rigid arms 404 and 406 that are pivotably connected to one another by a pin 408. The proximal ends of the arms 404 and 406 are respectively connected to a pair handle members 410 and 412, while the distal ends are respectively connected to a pair of clamp members 414 and 416. The clamp members 414 and 416 may be rigid or malleable and, if rigid, may be linear or have a pre-shaped curvature. A locking device 418 locks the clamp in the closed orientation, and prevents the clamp members 414 and 416 from coming any closer to one another than is illustrated in FIG. 34, thereby defining a predetermined spacing between the clamp members. The clamp 402 is also configured for use with a pair of soft, deformable inserts (not shown) that may be removably carried by the clamp members 414 and 416 and allow the clamp to firmly grip a bodily structure without damaging the structure. To that end, the clamp members 414 and 416 each include a slot 420 (FIGS. 35 and 36) that is provided with a sloped inlet area 422 and the inserts include mating structures that are removably friction fit within the slots. The exemplary tissue coagulation assembly 424 (FIG. 33 and 37) may be mounted on the clamp members in place of the inserts.

Figure 37:
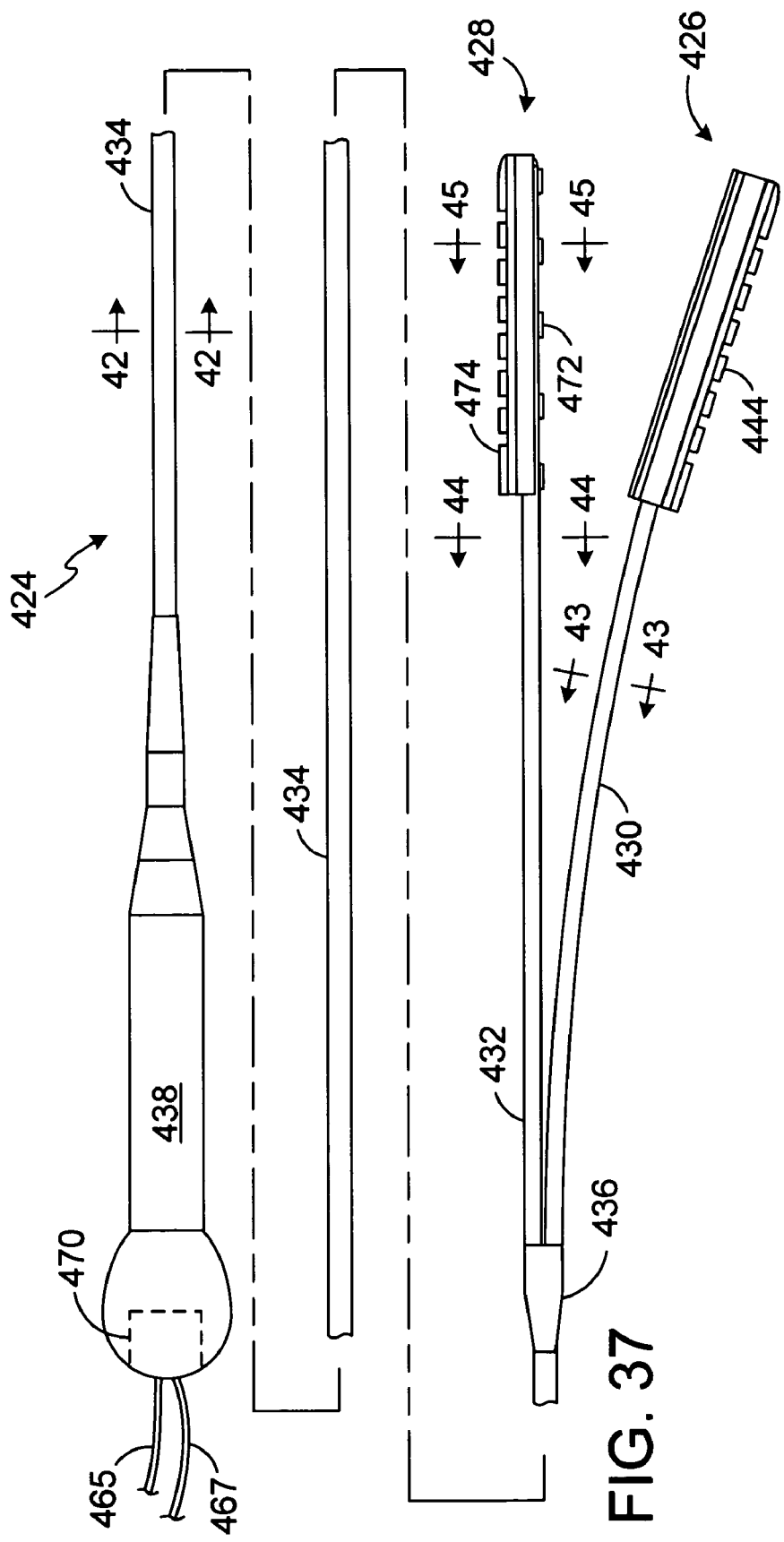
FIG. 37 is a plan view of a tissue coagulation assembly in accordance with a preferred embodiment of a present invention.

As illustrated in FIG. 37, the exemplary tissue coagulation assembly 424 includes a tissue coagulation device 426 that may be connected to one of the clamp members and a temperature sensor device 428 that may be connected to the other. The tissue coagulation device 426 and temperature sensor device 428 are respectively carried on support structures 430 and 432, which are connected to a tubular member 434 by a connector 436. The tubular member 434 is secured to a handle 438.

As illustrated for example in FIGS. 38-43, the exemplary tissue coagulation device 426 includes an insulation element 440, an energy transmission element 442 and a mounting device 444 that may be used to mount the tissue coagulation device on the clamp 402. A lumen 446 extends through the insulation element 440 and a plurality of electrodes 448 (or other energy emission elements) are carried on the portion of the support structure 430 that is located within the lumen. Tissue coagulation energy from the electrodes 448 is transferred to, and through, the energy transmission element 442 by electrically conductive fluid. To that end, the inner diameter of the lumen 446 is slightly greater than the outer diameter of the support structure 430 and a fluid transmission space 450 is defined between the support structure and the inner surface of the lumen 446. The insulation element 440 also includes a fluid slot 452 that extends from the fluid transmission space 450 to the energy transmission element 442. The longitudinal ends of the fluid transmission space are sealed by adhesive material 454, which is also used to secure the tissue coagulation device 426 to the support structure 430.

Referring to FIGS. 37-43, tissue coagulating energy and conductive fluid is supplied to the exemplary tissue coagulation device 426 by way of the support structure 430. To that end, the support structure 430 includes a wire lumen 456, a fluid infusion lumen 458, and a fluid ventilation lumen 460.

The distal ends of the lumens 456-460 are sealed by a plug 461. Fluid from the infusion lumen 458 enters the fluid transmission space 450 by way of an infusion aperture 458a (FIG. 39) and is enters the ventilation lumen 460 by way of a ventilation aperture 460a (FIG. 40). The tubular member 434 includes a wire lumen 462, a fluid infusion lumen 464, and a fluid ventilation lumen 466 that are connected to the corresponding lumens in the support structure 430 by the connector 436. Power wires 468 extend from the electrodes 448, and through the wire lumens 456 and 462, to a connector (such as a PC board) in a slot 470 formed in the handle 438 (FIG. 37). The connector (and electrodes 448) may be connected to the ESU 322 by way of the cable 324 and the connector 326 that may be received by the slot 470. The infusion and ventilation lumens 464 and 466 are connected to the tubes 465 and 467 within the handle 438, which are in turn connected to the tubes 308 and 310 from the fluid supply and control apparatus 300 by way of the illustrated stopcocks or other suitable devices.

The exemplary temperature sensor device 428 illustrated in FIGS. 33, 37, 44 and 45 includes a plurality of temperature sensors 472 that are carried on the support structure 432 and a mounting device 474 that may be used to mount the temperature sensor device on the clamp 402. The temperature sensors 472 (e.g. thermocouples or thermistors) are connected to signal wires 476 that extend through a lumen 477 in the support structure 432 and the wire lumen 462 in the tubular member 432. The signal wires 476 are also connected to the connector in the handle slot 470.

Turning to the manner in which the tissue coagulation device 426 is secured to the clamp 402, and referring to FIGS. 35, 36 and 38-41, the mounting device 444 includes a cup-shaped main portion 478 that is configured to receive the insulation element 440, and a connector 480 that is configured to removably mate with the slot 420 in the clamp 402. Adhesive may be used to secure the insulation element 440 within the main portion 478. The cup-shaped main portion 478 is substantially rigid and covers the substantial majority of the bottom and sides (when viewed in the orientation illustrated in FIGS. 39-41) of the insulation element 440. As a result, the main portion 478 prevents undesired deformation of the insulation element 440 during tissue coagulation procedures. The exemplary connector 480 is provided with a relatively thin portion 482 and a relatively wide portion 484, which may consist of a plurality of spaced members (as shown in FIG. 38) or an elongate unitary structure, in order to correspond to the shape of the slot 420 in the clamp 402.

Figure 45:
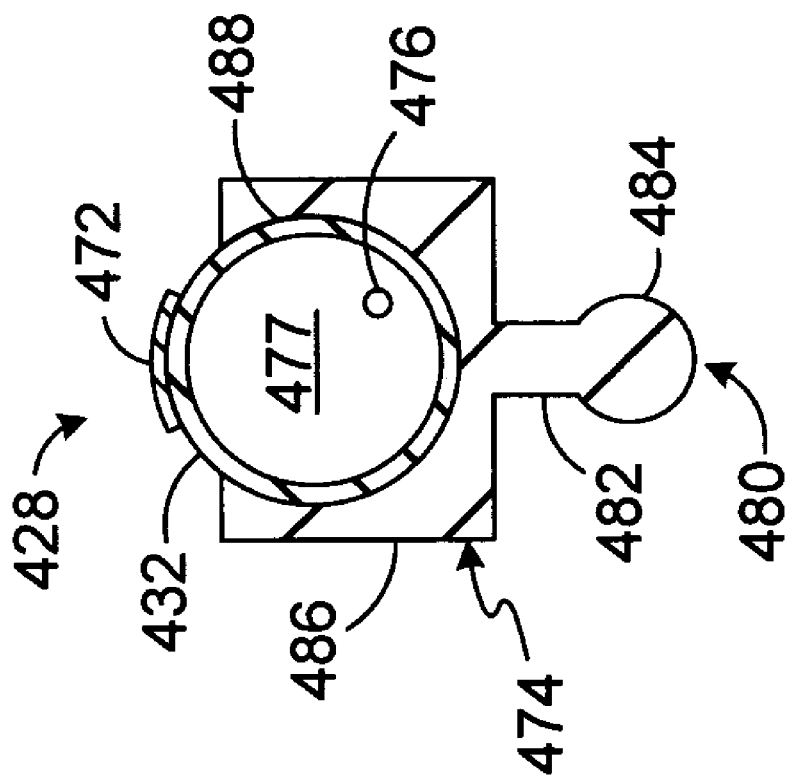
FIG. 45 is a section view taken along line 45-45 in FIG. 37.
Figure 44:
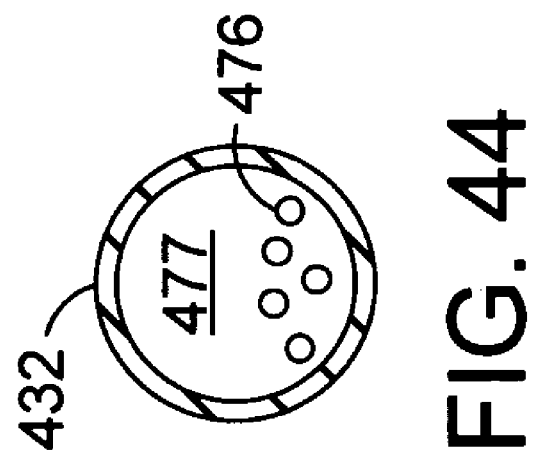
FIG. 44 is a section view taken along line 44-44 in FIG. 37.

With respect to the manner in which the temperature sensor device 428 is secured to the clamp 402, and referring to FIGS. 35, 36 and 45, the mounting device 474 includes a main portion 486 with a groove 488 that is configured to receive the support structure 432, and a connector 480 that mates with the clamp slot 420. The configuration of the groove 488 allows the support structure 432 to be snap fit into the main portion 486. Adhesive may also be used within the groove 488 to insure that the support structure 432 does not separate from the connector device 474.

Although the configuration of the tissue coagulation assembly 424 may vary from application to application to suit particular situations, the exemplary tissue coagulation assembly 424 is configured such that the energy transmission element 442 and the temperature sensors 472 will be parallel to one another as well as relatively close to one another (i.e. a spacing of about 1-10 mm) when the clamp 402 is in the closed orientation. Such an arrangement will allow the tissue coagulation assembly to firmly grip a bodily structure without cutting through the structure.

With respect to dimensions, the exemplary insulation element 440 is about ∂mm to °mm wide, along the surface that supports the energy transmission element 442, and about ∝mm to °mm thick. The fluid slot 452 will typically be about 1 to 3 mm wide. As a result, there will be a relatively wide insulation element portions (e.g. about ∝mm to ·mm) on either side of the fluid slot 452 that will insulate the tissue associated therewith from levels of coagulation energy that are great enough to coagulate tissue during a typical lesion formation procedure (i.e. about 50 to 180 seconds). The length of the exemplary insulation element 440 is about ≅to ζmm. Suitable materials for the insulation element 440 include the same materials that are used to form the insulation element 102 because the mounting device 444 is sufficiently rigid to provide a stable structure. With respect to the energy transmission element 442, the materials are the same as those discussed above with respect to the energy transmission element 104.

Turning to the materials used to form other aspects of the tissue coagulation assembly 424, the support structures 430 and 432 and tubular member 434 may be formed from PET or polyurethane tubing. The mounting devices 444 and 474 may be formed from polyurethane, nylon, Pebax®, ceramics, PES, PEEK, or metals such as aluminum, copper, stainless steel and Nitinol.

The exemplary clamp apparatus 400 may be reconfigured in a variety of ways. By way of example, but not limitation, one alternative tissue coagulation assembly includes a pair of the tissue coagulation device 426 with one carried on each of the clamp members 414 and 416. Here, temperature sensors may be provided on one or both of the tissue coagulation devices 426 in the manner described above with reference to FIGS. 32A and 32B. Additionally, the insulation element 440 and the mounting device 444 may be combined into an integrally formed, one-piece structure.

The exemplary clamp apparatus 400 may be used to form lesions in the following manner. The clamp members 414 and 416 may be positioned such that the tissue coagulation device 426 and temperature sensor device 428 are on opposite sides of a tissue structure. For example, the tissue coagulation device 426 and temperature sensor device 428 may be positioned on opposite sides of a single pulmonary vein or a pair of pulmonary veins. The clamp members 414 and 416 may then be brought into a completely closed orientation or, depending on the tissue structure, a slightly open orientation so long as the tissue structure is firmly held. After the fluid transmission space 450 and fluid slot 452 are filled with conductive fluid from the fluid supply and control apparatus 300, the power supply and control apparatus 320 may be used to supply coagulation energy to the electrodes 448. The temperature sensors 472 monitor the tissue temperature on the side of the target tissue structure opposite the energy transmission element 442.

The inventor herein has determined that temperature on the side of the target tissue structure opposite the energy transmission element 442 is indicative of lesion transmurality (i.e. whether or not a lesion that extends from one side of the target tissue structure to the other has been formed). More specifically, the inventor herein has determined that measured temperatures of about 50° C. to about 60° C. on the side of the tissue structure opposite the side that is in contact with the energy transmission element 442 for at least 1 second are indicative of the formation of a transmural lesion. The power supply and control apparatus 320 may, therefore, be configured to discontinue energy transmission when a predetermined temperature (e.g. a temperature between about 50° C. and about 60° C.) is measured by the temperature sensors 472 for at least 'seconds. Alternatively, or in addition, the power supply and control apparatus 320 may also be configured to provide an audible or visible indication that the predetermined temperature has been measured.

IV. Exemplary Probe Based Lesion Formation Apparatus

As illustrated for example in FIG. 46, an exemplary surgical system 30 in accordance with one embodiment of a present invention includes the fluid supply and control apparatus 300, the power supply and control apparatus 320, a surgical probe 500 having a shaft 502, a handle 504, and a plurality of electrodes 506, and an insulation element 600 that protects non-target tissue from unintended contact with the electrodes 506.

Turning first to the insulation element, the exemplary insulation element 600 illustrated in FIGS. 46-49 includes a main body 602 and a slot 604. The slot 604 is configured to receive the probe shaft 502, by way of an opening 606, and to removably secure the insulation element to the probe shaft. In other words, although the level of force required for removal of the insulation element 600 from the probe shaft 502 will be greater than that which will be experienced during a typical tissue coagulation procedure, it will be readily removable by the physician. The configuration of a slot 604 will, of course, depend on the configuration of the surgical probe with which it is intended to be used. The illustrated probe shaft 502 and electrodes 506 are generally cylindrical in shape and the slot 604 has a corresponding arcuate cross-sectional shape. The arc is preferably greater than 180 degrees so that the main body 602 will deflect when the probe shaft 502 is inserted into the slot 604 through the opening 606 and then snap back to hold the insulation element 600 in place.

The insulation element 600 also makes the surgical probe 500 "one directional" in that energy will only be transferred through the opening 606. Such an arrangement is more efficient that one in which the energy transfer can take place along the entire perimeter of the electrodes 506.

As illustrated for example in FIGS. 47 and 48, the exemplary insulation element 600 also includes side walls 608 that slant away from the opening 608. An insulation element with such a cross-section will be better able to flex when bent, especially when bent in a full or semi-circle.

With respect to materials, suitable materials for the insulation element 600 include flexible polymer (elastomer) open and closed cell foams. In those instance where open cell foams are used, the base member may include a sealing skin (not shown) to prevent fluid absorption. Flexible thermoplastics and thermoset polymers may also be employed. Materials that have a hardness rating of ≅to ±(Shore A) are preferred.

The overall dimensions of the insulation element 600 will depend upon the surgical probe with which it is intended to be used. In the exemplary implementation, the length of the insulation element 600 is slightly longer that the distance between the proximal end of the proximal-most electrode 506 and the distal end of distal-most electrode, i.e. about ..to +cm. The overall width of the insulation element 600 is about ∂to °mm, while the width of the opening is preferably 606 is about 1 to 3 mm. The aspect ratio, i.e. the width to thickness (or height) ratio, is about 2-3 to 1 and, accordingly, the thickness of the exemplary insulation element 600 is about 'to mm.

In alternative configurations, adhesive may be used to permanently secure the insulation element 600 to the surgical probe 500, especially in those instances where the arc of the slot 604 is less than 180 degrees. Adhesive may be used for this purpose.

Insulation elements in accordance with the present inventions may also be linear prior to the bending of the shaft on which they are mounted (as illustrated in FIGS. 46-49) or pre-shaped. Pre-shaping may be accomplished by molding the insulation element with a particular shape. The pre-shaping may also be accomplished by added pre-shaped elements, such as the plurality of polymer, composite or metal members reinforcing members 194 illustrated in FIG. 19I or the pre-shaped reinforcing members 196 (with or without the removable stylet 198) illustrated in FIGS. 20-22.

Turning to the exemplary surgical probe 500, and referring to FIGS. 46 and 50-52, the shaft 502 is relatively short (e.g. about 'cm to about cm in length) and relatively stiff. In other words, the shaft is rigid, malleable, or somewhat flexible. A rigid shaft cannot be bent. A malleable shaft is a shaft that can be readily bent by the physician to a desired shape, without springing back when released, so that it will remain in that shape during the surgical procedure. Thus, the stiffness of a malleable shaft must be low enough to allow the shaft to be bent, but high enough to resist bending when the forces associated with a surgical procedure are applied to the shaft. A somewhat flexible shaft will bend and spring back when released. However, the force required to bend the shaft must be substantial.

In the illustrated embodiment, the shaft 502 consists of a proximal portion 508, including a malleable hypotube 510 and an outer polymer coating 512, and distal portion 514, including a malleable mandrel 516 and a multi-lumen electrically non-conductive outer structure 518. The proximal portion 508 will typically be about 'to +cm in length, while the distal portion will typically be about to αcm in length. The proximal end of the malleable mandrel 516 is secured to the inner surface of the distal end of the hypotube 510 and the distal end of the malleable mandrel is secured to a tip member 520. The exemplary tip member 520 is provided with a suture aperture 521 (FIG. 50). If desired, physicians may pass a suture through the aperture 521 and use the suture to pull the shaft 502 around a body structure.

The exemplary surgical probe 500 is a fluid cooled surgical probe and, as illustrated in FIGS. 51 and 52, the electrically non-conductive outer structure 518 includes fluid inlet and outlet lumens 522 and 524, power and signal wire lumens 526 and 528, a central lumen 530 for the mandrel 516. To that end, the tip member 520 includes a connection lumen (not shown) that connects the inlet lumen 522 to the outlet lumen 524, as well as a pair of plugs (not shown) to seal the power and signal wire lumens 526 and 528. Heat from the electrodes 506 is transferred through the outer structure 518 to fluid that is flowing through the inlet and outlet lumens 522 and 524. Accordingly, in addition to being electrically non-conductive, the material used to form the outer structure 518 should be relatively high in thermal conductivity. As used herein, "relatively high" thermal conductivity is at least about 1 W/m·K and preferably ranges from about 1 to about 10 W/m·K. Suitable electrically non-conductive, thermally conductive thermoplastics for the outer structure 518 include flexible thermoplastic polymer materials, such as nylon or polyurethane, which are filled with a filler that promotes heat transfer. Suitable fillers include graphite, aluminum, tungsten and ceramic powders. Another suitable filler is Carborundum CarboTherm™ boron nitride powder manufactured by Saint-Gobain in Cavaillon, France.

In addition to the aforementioned fillers, heat transfer may be promoted by minimizing the thickness of the electrically non-conductive material between the lumens 522 and 524 and the electrodes 506 and by maximizing the cross-sectional area of the inlet and outlet lumens. With respect to the outer structure 518 illustrated in FIG. 52, for example, in an implementation where the outer diameter of the outer structure is about 8 French (2.66 mm), the thickness of the outer wall 532 between the electrodes 506 and the inlet and outlet lumens 522 and 524 will be about 0.08 mm to about 0.36 mm. It should be noted that when the outer wall thickness is about 0.02 mm or less, materials with less than "relatively high" thermal conductivities, such as Pebax® material and polyurethane, may also be used for the outer structure 518.

As illustrated for example in FIG. 46, fluid may be supplied to the surgical probe 500 by way of an infusion tube 534, which is connected to the inlet lumen 522. The infusion tube 534 extends through an aperture in the handle 504 and is provided with stop-cock, which may be connected to the tube 308 that is associated with the fluid supply and control apparatus outlet port 304. Similarly, a ventilation tube 536 is connected to the outlet lumen 524 and extends through an aperture in the handle 504. The ventilation tube 536 may be connected to the tube 310 that is associated with the inlet port 306 on the fluid supply and control apparatus 300.

The cooling fluid is not limited to any particular fluid. Preferably, however, the fluid will be a low or electrically non-conductive fluid such as sterile water or 0.9% saline solution in those instances where the fluid will not be used to transmit current to tissue. A suitable fluid inlet temperature is about 0 to 25° C. and the fluid supply and control apparatus 300 may be provided with a suitable cooling system, if desired, to bring the temperature of the fluid down to the desired level. In a seven electrode embodiment where 150 W is being supplied to the electrodes 506, for example, a suitable constant fluid flow rate is about =ml/min to about °ml/min.

Although the present inventions are not limited to any particular type or number, the exemplary probe 500 includes seven spaced electrodes 506. The spaced electrodes 506 are preferably in the form of wound, spiral closed coils. The coils are made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility. Preferred coil electrodes are disclosed in U.S. Pat. Nos. 5,797,905 and 6,245,068.

Alternatively, the electrodes 506 may be in the form of solid rings of conductive material, like platinum, or can comprise a conductive material, like platinum-iridium or gold, coated upon the device using conventional coating techniques or an ion beam assisted deposition (IBAD) process. For better adherence, an undercoating of nickel, silver or titanium can be applied. The electrodes can also be in the form of helical ribbons. The electrodes can also be formed with a conductive ink compound that is pad printed onto a non-conductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks. Open coil electrodes may also be employed.

The exemplary flexible electrodes 506 are preferably about 4 mm to about 20 mm in length. In the preferred embodiments, the electrodes are 12.5 mm in length with 1 mm to 3 mm spacing, which will result in an energy transmission region that is about 1 cm to about 14 cm in length and the creation of continuous lesion patterns in tissue when coagulation energy is applied simultaneously to adjacent electrodes. For rigid electrodes, the length of the each electrode can vary from about 2 mm to about 10 mm. Using multiple rigid electrodes longer than about 10 mm each adversely effects the overall flexibility of the device, while electrodes having lengths of less than about 2 mm do not consistently form the desired continuous lesion patterns.

The electrodes 506 are electrically coupled to individual power wires 538 that pass from the power wire lumen 526, and through a power wire tube 540, to a PC board or other suitable connector that is associated with a slot 542 in the handle 504. A plurality of temperature sensors 544, such as thermocouples or thermistors, may be located on, under, abutting the longitudinal end edges of, or in between, the electrodes 506. A reference thermocouple (not shown) may also be provided. In the exemplary implementation, temperature sensors 544 are located at both longitudinal ends of each electrode 506. The temperature sensors 544 are connected to the PC board by signal wires 546, which pass through the signal wire lumen 528 and a signal wire tube 548. The temperature sensors 544 are also located within a linear channel 550 that is formed in the non-conductive outer structure 518. The linear channel 550 insures that the temperature sensors will all face in the same direction (e.g. facing tissue) and be arranged in linear fashion. Preferably, the probe 500 will be secured to the insulation element 600 in such a manner that the temperature sensors 544 and linear channel 550 will be aligned with the slot 604 and will face tissue during use.

Additional details concerning fluid cooled surgical probes similar to that described above are presented in U.S. Patent App. Pub. No. 2003/0078644, which is entitled "Apparatus for Supporting Diagnostic and Therapeutic Elements in Contact With Tissue Including Dual Lumen Cooling Device" and incorporated herein by reference.

Although the inventions disclosed herein have been described in terms of the preferred embodiments above, numerous modifications and/or additions to the above-described preferred embodiments would be readily apparent to one skilled in the art. By way of example, but not limitation, the present inventions include systems that comprise one or both of a fluid supply and control apparatus and a power supply and control apparatus in addition to the various apparatus and/or clamps claimed below. It is intended that the scope of the present inventions extend to all such modifications and/or additions and that the scope of the present inventions is limited solely by the claims set forth below.

I claim:

1. A tissue coagulation device, comprising:
   an insulation element comprising a lumen and a fluid slot;
   a support structure located within the lumen of the insulation element, the support structure comprising a wire lumen, a fluid infusion lumen, a fluid ventilation lumen, an infusion aperture, and a ventilation aperture;
   an electrode disposed on the support structure; and
   an energy transmission element coupled with the insulation element;
   wherein a fluid transmission space is defined between the support structure and an inner surface of the lumen of the insulation element, the fluid transmission space being circumferentially disposed around at least a portion of an outer surface of the support structure,
   wherein the fluid slot extends from the fluid transmission space to the energy transmission element,
   wherein the infusion aperture of the support structure allows fluid to enter the fluid transmission space from the fluid infusion lumen, and wherein the ventilation aperture of the support structure allows fluid to enter the fluid ventilation lumen from the fluid transmission space.

2. The tissue coagulation device of claim 1, further comprising a power wire disposed within the wire lumen of the support structure, wherein the power wire is coupled with the electrode.

3. The tissue coagulation device of claim 1, further comprising an electrically conductive fluid disposed within the fluid transmission space, wherein the electrically conductive fluid is configured to transfer tissue coagulation energy from the electrode to the energy transmission element.

4. The tissue coagulation device of claim 3, wherein the energy transmission element comprises an electrically non-conductive hydrophilic conductive polymer film comprising pores that allow ionic transport in response to an applied RF field.

5. The tissue coagulation device of claim 1, further comprising a mounting device coupled with the insulation element, wherein the mounting device comprises a connector that is configured to removably mate with a clamp.

6. The tissue coagulation device of claim 5, wherein the clamp comprises a malleable clamp member, and the tissue coagulation device is removably coupled with the malleable clamp member via the mounting device.

7. The tissue coagulation device of claim 1, wherein the lumen comprises an inner diameter, the support structure comprises an outer diameter, and the inner diameter of the lumen is greater than the outer diameter of the support structure.

8. A method of performing a tissue coagulation procedure on a patient, comprising:
  contacting a tissue of the patient with a tissue coagulation device, wherein the tissue coagulation device comprises:
    an insulation element comprising a lumen and a fluid slot;
    a support structure located within the lumen of the insulation element, the support structure comprising a wire lumen, a fluid infusion lumen, a fluid ventilation lumen, an infusion aperture, and a ventilation aperture;
    an electrode disposed on the support structure;
    an energy transmission element coupled with the insulation element;
    wherein a fluid transmission space is defined between the support structure and an inner surface of the lumen of the insulation element, the fluid transmission space being circumferentially disposed around at least a portion of an outer surface of the support structure,
    wherein the fluid slot extends from the fluid transmission space to the energy transmission element,
    wherein the infusion aperture of the support structure allows fluid to enter the fluid transmission space from the fluid infusion lumen, and
    wherein the ventilation aperture of the support structure allows fluid to enter the fluid ventilation lumen from the fluid transmission space, and
  delivering a coagulation energy to the tissue of the patient with the tissue coagulation device via the electrode.

9. The method of claim 8, wherein the tissue coagulation device further comprises a power wire disposed within the wire lumen of the support structure, and wherein the power wire is coupled with the electrode.

10. The method of claim 8, wherein the tissue coagulation device further comprises an electrically conductive fluid disposed within the fluid transmission space, and wherein the electrically conductive fluid is configured to transfer tissue coagulation energy from the electrode to the energy transmission element.

11. The method of claim 10, wherein the energy transmission element comprises an electrically non-conductive hydrophilic conductive polymer film comprising pores that allow ionic transport in response to an applied RF field.

12. The method of claim 8, wherein the tissue coagulation device further comprises a mounting device coupled with the insulation element, and wherein the mounting device comprises a connector that is configured to removably mate with a clamp.

13. The method of claim 12, wherein the clamp comprises a malleable clamp member, and the tissue coagulation device is removably coupled with the malleable clamp member via the mounting device.

14. The method of claim 8, wherein the lumen comprises an inner diameter, the support structure comprises an outer diameter, and the inner diameter of the lumen is greater than the outer diameter of the support structure.

15. The tissue coagulation device of claim 1, wherein the energy transmission element is coupled directly with the insulation element.

16. The tissue coagulation device of claim 1, wherein the fluid transmission space is between the entire outer surface of the support structure and the inner surface of the lumen of the insulation element, the fluid transmission space being circumferentially disposed around the entire outer surface of the support structure.

17. The tissue coagulation device of claim 1, wherein the infusion aperture provides fluid communication between the fluid infusion lumen of the support structure and the fluid transmission space disposed within the insulation element.

18. The tissue coagulation device of claim 1, wherein the ventilation aperture of the support structure allows fluid to enter the fluid ventilation lumen directly from the fluid transmission space.

19. The tissue coagulation device of claim 1, wherein the fluid slot allows fluid within the fluid transmission space to contact the energy transmission element.

* * * * *